US009857357B2

(12) United States Patent
Nagata et al.

(10) Patent No.: US 9,857,357 B2
(45) Date of Patent: Jan. 2, 2018

(54) METHOD OF SCREENING MODULATOR OF XKR8

(71) Applicant: KYOTO UNIVERSITY, Kyoto (JP)

(72) Inventors: Shigekazu Nagata, Kyoto (JP); Jun Suzuki, Suita (JP)

(73) Assignee: KYOTO UNIVERSITY, Kyoto (JP)

( * ) Notice: Subject to any disclaimer, the term of this patent is extended or adjusted under 35 U.S.C. 154(b) by 63 days.

(21) Appl. No.: 14/440,968

(22) PCT Filed: Nov. 13, 2013

(86) PCT No.: PCT/JP2013/080692
§ 371 (c)(1),
(2) Date: May 6, 2015

(87) PCT Pub. No.: WO2014/077279
PCT Pub. Date: May 22, 2014

(65) Prior Publication Data
US 2015/0301024 A1 Oct. 22, 2015

Related U.S. Application Data

(60) Provisional application No. 61/726,147, filed on Nov. 14, 2012.

(51) Int. Cl.
G01N 33/50 (2006.01)

(52) U.S. Cl.
CPC ..... *G01N 33/5011* (2013.01); *G01N 33/5008* (2013.01); *G01N 2405/04* (2013.01); *G01N 2500/10* (2013.01)

(58) Field of Classification Search
CPC ........... G01N 2405/04; G01N 33/5008; G01N 2500/10; G01N 33/5011
See application file for complete search history.

(56) References Cited

U.S. PATENT DOCUMENTS

| 2003/0129722 A1 | 7/2003 | Wiedmer et al. |
| 2006/0172958 A1 | 8/2006 | Lee et al. |

FOREIGN PATENT DOCUMENTS

| WO | 2012/029855 | 3/2012 |

OTHER PUBLICATIONS

Bevers EM et al., "Getting to the Outer Leaflet: Physiology of Phosphatidylserine Exposure at the Plasma Membrane", Physiol. Rev., 2016, vol. 96, pp. 605-645.*
Extended European Search Report dated Apr. 6, 2016 in corresponding European patent application No. 13 85 4768.
Suzuki J. et al., "Exposure of phosphatidylserine by Xk-related protein family members during apoptosis", J. Biol. Chem., vol. 289, No. 44, Oct. 31, 2014, pp. 30257-30267, XP552060614.

Segawa K. et al., "An apoptotic 'Eat Me' signal: Phosphatidylserine exposure", Trends in Cell Biology, vol. 25, No. 11, Nov. 2015, pp. 639-650, XP029321465.
International Search Report dated Jan. 28, 2014 in International Application No. PCT/JP2013/080692.
International Preliminary Report on Patentability dated May 19, 2015 in International Application No. PCT/JP2013/080692.
Suzuki Jun et al., "Xk-Related Protein 8 and CED-8 Promote Phosphatidylserine Exposure in Apoptotic Cells", Science, Jul. 26, 2013, vol. 341, No. 6144, pp. 403-406.
Marino Guillermo et al., "Mechanisms of apoptotic phosphatidylserine exposure", Cell Research, Nov. 2013, vol. 23, No. 11, pp. 1247-1248, Electronic Publication Date: Aug. 27, 2013.
Calenda Giulia et al., "Identification of two new members, XPLAC and XTES, of the XK family", Gene, Mar. 29, 2006, vol. 370, pp. 6-16, Electronic Publication Date: Jan. 20, 2006.
Jacobson, M. D., Weil, M., & Raff, M. C., "Programmed Cell Death in Animal Development", Cell 88, pp. 347-354 (1997).
Vaux, D. L. & Korsmeyer, S. J., "Cell Death in Development", Cell 96, pp. 245-254 (1999).
Nagata, S., "Apoptosis by Death Factor", Cell 88, pp. 355-365 (1997).
Strasser, A., O'Connor, L., & Dixit, V. M., "Apoptosis Signaling", Annu. Rev. Biochem. 69, pp. 217-245 (2000).
Nagata, S., "DNA Degradation in Development and Programmed Cell Death", Annu. Rev. Immunol, 23, pp. 853-875 (2005).
Enari, M. et al., "A caspase-activated DNase that degrades DNA during apoptosis and its inhibitor ICAD", Nature 391, pp. 43-50 (1998).
Coleman, M. et al., "Membrane blebbing during apoptosis results from caspase-mediated activation of ROCK I", Nat. Cell Biol. 3, pp. 339-345 (2001).
Sebbagh, M. et al., "Caspase-3-mediated cleavage of ROCK I induces MLC phosphorylation and apoptotic membrane blebbing", Nat. Cell Biol. 3, pp. 346-352 (2001).
Fadok, V. A. et al., "Exposure of Phosphatidylserine on the Surface of Apoptotic Lymphocytes Triggers Specific Recognition and Removal of Macrophages", J. Immunol. 148, pp. 2207-2216 (1992).
Leventis, P. A. & Grinstein, S., "The Distribution and Function of Phosphatidylserine in Cellular Membranes", Annu. Rev. Biophys. 39, pp. 407-427 (2010).
Ravichandran, K. S. & Lorenz, U., "Engulfment of apoptotic cells: signals for a good meal", Nat. Rev. Immunol. 7, pp. 964-974 (2007).
Nagata, S., Hanayama, R., & Kawane, K., "Autoimmunity and the Clearance of Dead Cells", Cell 140, pp. 619-630 (2010).
Zwaal, R., Comfurius, P., & Bevers, E., "Lipid-protein interactions in blood coagulation", Biochim. Biophys. Acta 1376, pp. 433-453 (1998).
Bevers, E. & Williamson, P., "Phospholipid scramblase: An update", FEBS Lett. 584, pp. 2724-2730 (2010).
Suzuki, J., Umeda, M., Sims, P. J., & Nagata, S., "Calcium-dependent phospholipid scrambling by TMEM16F", Nature 468, pp. 834-838 (2010).
Williamson, P. et al., "Phospholipid Scramblase Activation Pathways in Lymphocytes", Biochemistry 40, pp. 8065-8072 (2001).
Fadeel, B. et al., "Phosphatidylserine Exposure during Apoptosis is a Cell-Type-Specific Event and Does Not Correlate with Plasma Membrane Phospholipid Scramblase Expression", Biochem. Biophys. Res. Commun. 266, pp. 504-511 (1999).

(Continued)

*Primary Examiner* — Satyendra K Singh
(74) *Attorney, Agent, or Firm* — Wenderoth, Lind & Ponack, L.L.P.

(57) ABSTRACT

The disclosure relates to a method of screening a modulator of Xkr8, comprising the steps of:
(1) contacting Xkr8-expressing cells with a candidate of the modulator, and
(2) selecting the candidate when the candidate alters distribution of a phospholipid in plasma membrane of the cells.

5 Claims, 27 Drawing Sheets

(56) References Cited

OTHER PUBLICATIONS

Fadok, V. A., de Cathelineau, A., Daleke, D. L., Henson, P. M., & Bratton, D. L., "Loss of Phospholipid asymmetry and Surface Exposure of Phosphatidylserine Is Required for Phagocytosis of Apoptotic Cells by Macrophages and Fibroblasts", J. Biol. Chem. 276, pp. 1071-1077 (2001).

Herman, J. G., Graff, J. R., Myohanen, S., Nelkin, B. D., & Baylin, S. B., "Methylation-specific PCR: a novel PCR assay for methylation status of CpG islands", Proc. Natl. Acad. Sci. USA 93, pp. 9821-9826 (1996).

Balasubramanian, K. & Schroit, A., "Aminophospholipid Asymmetry: A Matter of Life and Death", Annu. Rev. Physiol. 65, 701-734 (2003).

Emoto, K., Toyama-Sorimachi, N., Karasuyama, H., Inoue, K., & Umeda, M., "Exposure of Phosphatidylethanolamine on the Surface of Apoptotic Cells", Exp. Cell Res. 232, pp. 430-434 (1997).

Calenda, G. et al., "Identification of two new members, XPLAC and XTES, of the XK family", Gene 370, pp. 6-16 (2006).

Timmer, J. C. & Salvesen, G. S., "Caspase substrates", Cell Death Differ. 14, 66-72 (2007).

Martin, S. J., Finucane, D. M., Amarante-Mendes, G. P., O'Brien, G. A., & Green, D. R., "Phosphatidylserine Externalization during CD95-induced Apoptosis of Cells and Cytoplasts Requires ICE/CED-3 Protease Activity", J. Biol. Chem. 271, pp. 28753-28756 (1996).

Giraudo, C. G. & Maccioni, H. J. F., "Endoplasmic reticulum Export of Glycosyltransferases Depends on Interaction of a Cytoplasmic Dibasic Motif with Sar1", Mol. Biol. Cell. 14, pp. 3753-3766 (2003).

Barlowe, C., "Signals for COPII-dependent export from the ER: what's the ticket out?", Trends Cell Biol. 13, pp. 295-300 (2003).

Ho, M. et al., "Isolation of the Gene for McLeod Syndrome That Encodes a Novel Membrane Transport Protein", Cell 77, pp. 869-880 (1994).

Russo, D., Redman, C., & Lee, S., "Association of XK and Kell Blood Group Proteins", The Journal of biological chemistry 273, pp. 13950-13956 (1998).

Schoenwaelder, S. M. et al., "Two distinct pathways regulate platelet phosphatidylserine exposure and procoagulant function", Blood 114, pp. 663-666 (2009).

Ricci, J.-E. et al., "Disruption of Mitochondrial Function during Apoptosis Is Mediated by Caspase Cleavage of the p75 Subunit of Complex I of the Electron Transport Chain", Cell 117, pp. 773-786 (2004).

Gleiss, B., Gogvadze, V., Orrenius, S., & Fadeel, B., "Fas-triggered phosphatidylserine exposure is modulated by intracellular ATP", FEBS Lett. 519, pp. 153-158 (2002).

Fadeel, B. & Orrenius, S., "Apoptosis: a basic biological phenomenon with wide-ranging implications in human disease", J. Inter. Med. 258, pp. 479-517 (2005).

Sandilos, J. K. et al., "Pannexin 1, an ATP Release Channel, Is Activated by Caspase Cleavage of Its Pore-associated C-terminal Autoinhibitory Region", J. Biol. Chem. 287, pp. 11303-11311 (2012).

Chekeni, F. B. et al., "Pannexin 1 channels mediate 'find-me' signal release and membrane permeability during apoptosis", Nature 467, pp. 863-867 (2010).

Bratton, D. et al., "Appearance of Phosphatidylserine on Apoptotic Cells Requires Calcium-mediated Nonspecific Flip-Flop and Is Enhanced by Loss of the Aminophospholipid Translocase", J. Biol. Chem. 272, pp. 26159-26165 (1997).

Hampton, M., Vanags, D., Pörn-Ares, M., & Orrenius, S., "Involvement of extracellular calcium in phosphatidylserine exposure during apoptosis", FEBS Lett. 399, pp. 277-282 (1996).

van den Eijnde, S. et al., "Cell surface exposure of phosphatidylserine during apoptosis is phylogenetically conserved", Apoptosis 3, pp. 9-16 (1998).

Venegas, V. & Zhou, Z., "Two Alternative Mechanisms That Regulate the Presentation of Apoptotic Cell Engulfment Signal in Caenorhabditis elegans", Mol. Biol. Cell 18, pp. 3180-3192 (2007).

Ellis, R. E., Jacobson, D. M., & Horvitz, H. R., "Genes Required for the Engulfment of Cell Corpses During Programmed Cell Death in Caenorhabditis elegans" Genetics 129, pp. 79-94. (1991).

Stanfield, G. & Horvitz, H., "The ced-8 Gene Controls the Timing of Programmed Cell Deaths in C. elegans", Mol. Cell 5, pp. 423-433 (2000).

Munoz, L. E., Lauber, K., Schiller, M., Manfredi, A. A., & Herrmann, M., "The role of defective clearance of apoptotic cells in systemic autoimmunity", Nat. Rev. Rheumatol. 6, pp. 280-289 (2010).

Franks, A. L. & Slansky, J. E., "Multiple Associations Between a Broad Spectrum of Autoimmune Diseases, Chronic Inflammatory Diseases and Cancer", Anticancer Res. 32, pp. 1119-1136 (2012).

Yoshida, H. et al., "Phosphatidylserine-dependent engulfment by macrophages of nuclei from erythroid precursor cells", Nature 437, pp. 754-758 (2005).

Connor, J., Pak, C. C., & Schroit, A. J., "Exposure of Phosphatidylserine in the Outer Leaflet of Human Red Blood Cells", Relationship to cell density, cell age, and clearance by mononuclear cells. J. Biol. Chem. pp. 269, 2399-2404 (1994).

Stowell, S. R. et al., "Galectin-1 Induces Reversible Phosphatidylserine Exposure at the Plasma Membrane", Mol. Biol. Cell 20, pp. 1408-1418 (2009).

Van den Eijnde, S. et al., "Transient expression of phosphatidylserine at cell-cell contact areas is required for myotube formation", J. Cell Sci. 114, pp. 3631-3642 (2001).

Gadella, B. & Harrison, R., "Capacitation Induces Cyclic Adenosine 3',5'-Monophosphate-Dependent, but Apoptosis-Unrelated, Exposure of Aminophospholipids at the Apical Head Plasma Membrane of Boar Sperm Cells", Biol. Reprod. 67, pp. 340-350 (2002).

Marguet, D., Luciani, M. F., Moynault, A., Williamson, P., & Chimini, G., "Engulfment of apoptotic cells involves the redistribution of membrane phosphatidylserine on phagocyte and prey", Nat. Cell Biol. 1, pp. 454-456 (1999).

Imao, T. & Nagata, S., "Apaf-1 - and Caspase-8-independent apoptosis", Cell Death Differ, in press (2012).

Palacios, R. & Steinmetz, M., "Il-3-Dependent Mouse Clones That Express B-220 Surface Antigen, Contain Ig Genes in Germ-Line Configuration, and Generate B Lymphocytes in Vivo", Cell 41, pp. 727-734 (1985).

Tucker, K. A., Lilly, M. B., Heck, L., & Rado, T. A., "Characterization of a New Human Diploid Myeloid Leukemia Cell Line (PLB-985) With Granulocytic and Monocytic Differentiating Capacity", Blood 70, pp. 372-378 (1987).

Morita, S., Kojima, T., & Kitamura, T., "Plat-E: an efficient and stable system for transient packaging of retroviruses", Gene Ther. 7, pp. 1063-1066 (2000).

Fukunaga, R., Ishizaka-Ikeda, E., & Nagata, S., "Purification and Characterization of the Receptor for Murine Granulocyte Colony-stimulating Factor", J. Biol. Chem. 265, pp. 14008-14015 (1990).

Shiraishi, T. et al., "Increased cytotoxicity of soluble Fas ligand by fusing isoleucine zipper motif", Biochem. Biophys. Res. Commun. 322, pp. 197-202 (2004).

Kitamura, T. et al., "Retrovirus-mediated gene transfer and expression cloning: powerful tools in functional genomics", Exp. Hematol. 31, pp. 1007-1014 (2003).

Higuchi, R., "Recombinant PCR" in PCR protocols: A guide to methods and applications (Academic Press, San Diego, 1990), pp. 177-188.

Kontgen, F., Suss, G., Stewart, C., Steinmetz, M., & Bluethmann, H., "Targeted disruption of the MHC class II Aa gene in C57BL/6 mice", Int. Immunol. 5, pp. 957-964 (1993).

Kanki, H., Suzuki, H., & Itohara, S., "High-efficiency CAG-FLPe Deleter Mice in C57BL/6J Background", Exp. Anim. 55, pp. 137-141 (2006).

Cattermole, J. A. et al., "Isolation of Murine Fetal Thymus Cell Lines After Infection With Recombinant Retroviruses Containing the v-myc and v-Ha-ras Oncogenes", J. Immunol. 142, 3746-3753 (1989).

Akagi, T., Sasai, K., & Hanafusa, H., "Refractory nature of normal human diploid fibroblasts with respect to oncogene-mediated transformation", Proc. Natl. Acad. Sci. USA 100, pp. 13567-13572 (2003).

(56) References Cited

OTHER PUBLICATIONS

Watson, J. D., Morrissey, P. J., Namen, A. E., Conlon, P. J., & Widmer, M. B., "Effect of IL-7 on the Growth of Fetal Thrmocytes in Culture", J. Immunol. 143, pp. 1215-1222 (1989).

Watanabe-Fukunaga, R. et al., "The cNA Structure, Expression, and Chromosomal Assignment of the Mouse Fas Antigen", J. Immunol. 148, pp. 1274-1279 (1992).

Ogasawara, J. et al., "Lethal effect of the anti-Fas antibody in mice", Nature 364, pp. 806-809 (1993).

Aoki, Y., Uenaka, T., Aoki, J., Umeda, M., & Inoue, K., "A Novel Peptide Probe for Studying the Transbilayer Movement of Phosphatidylethanolamine", J. Biochem. 116, pp. 291-297 (1994).

\* cited by examiner

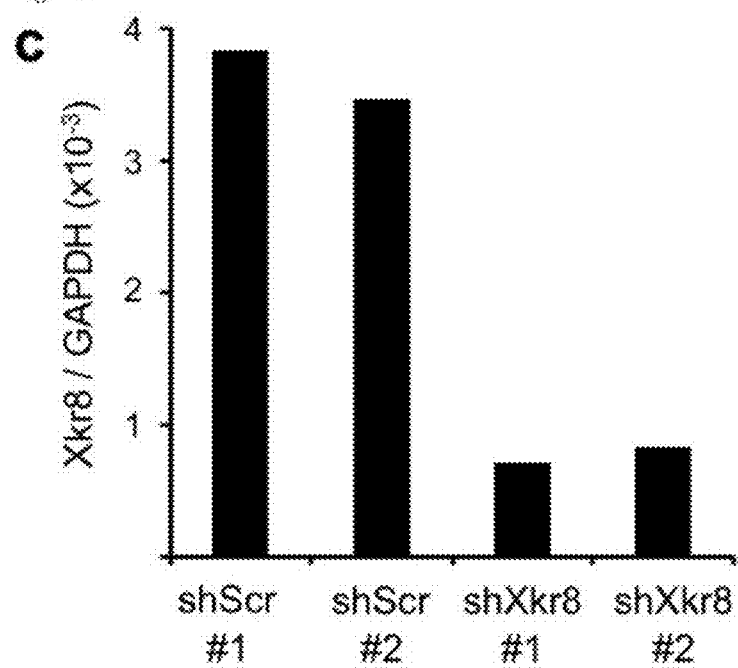

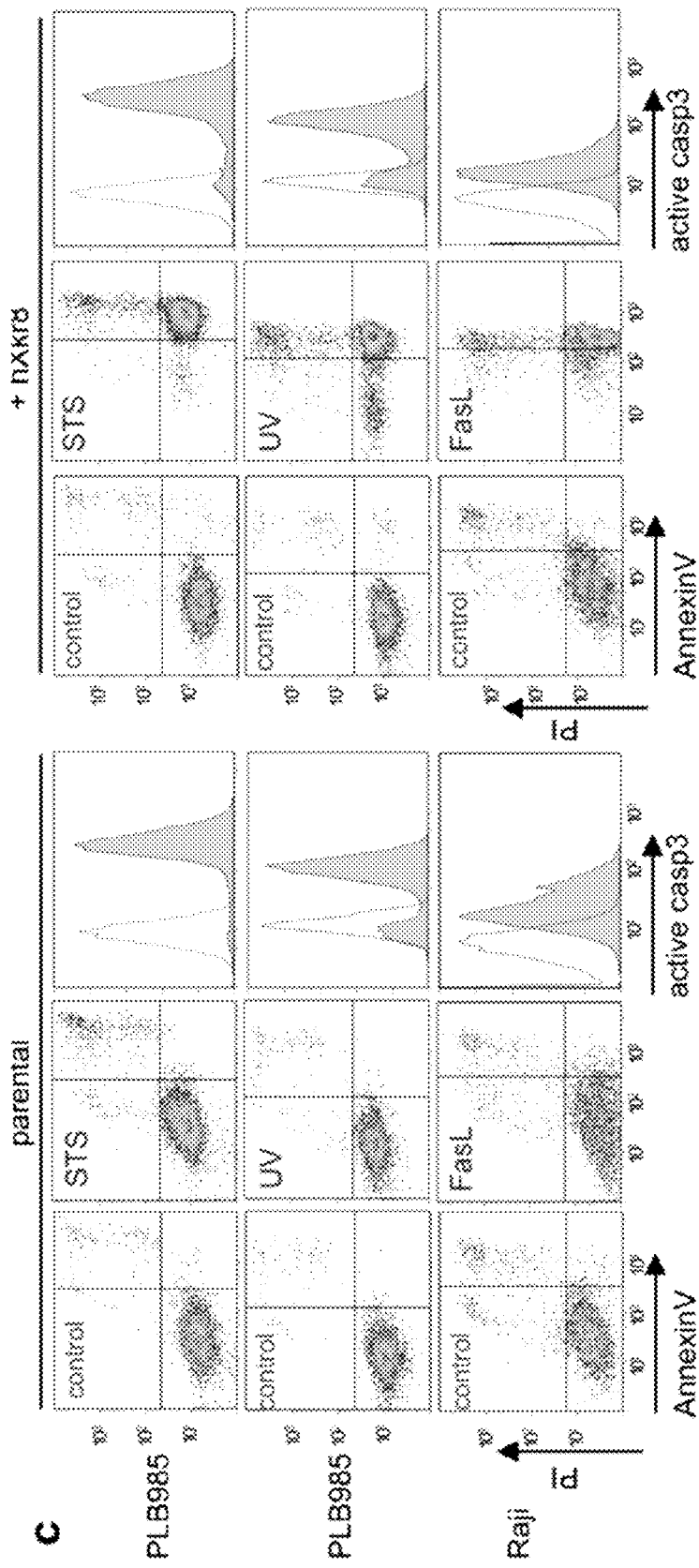

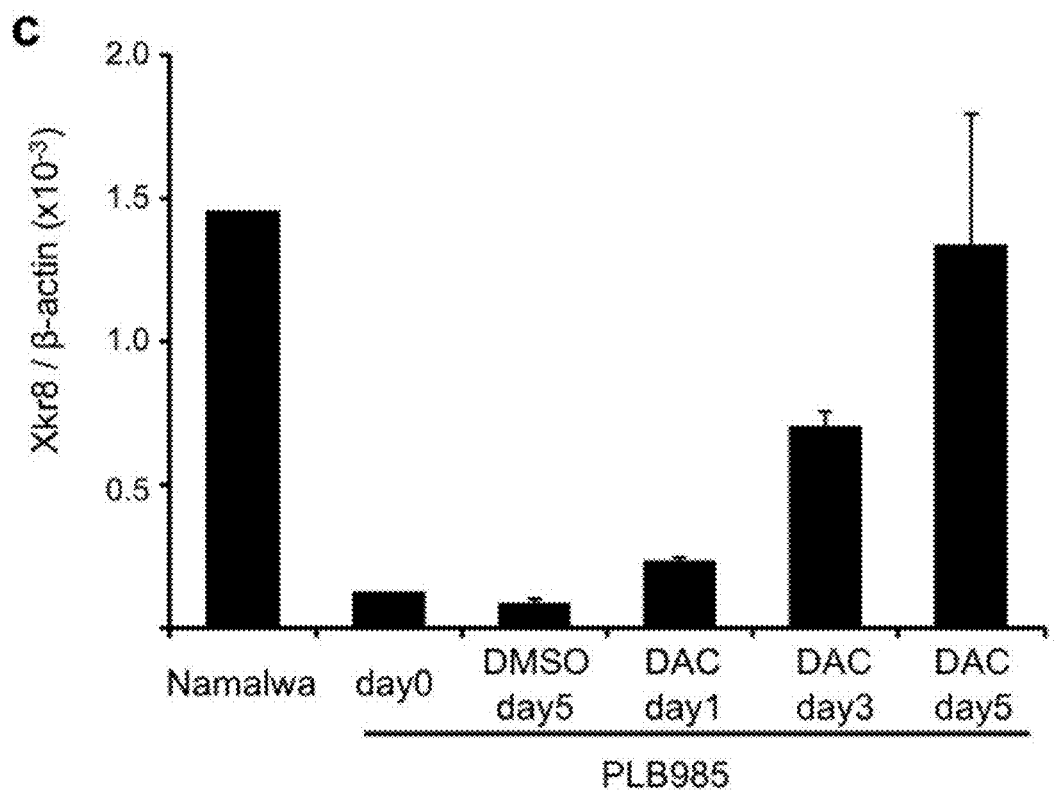

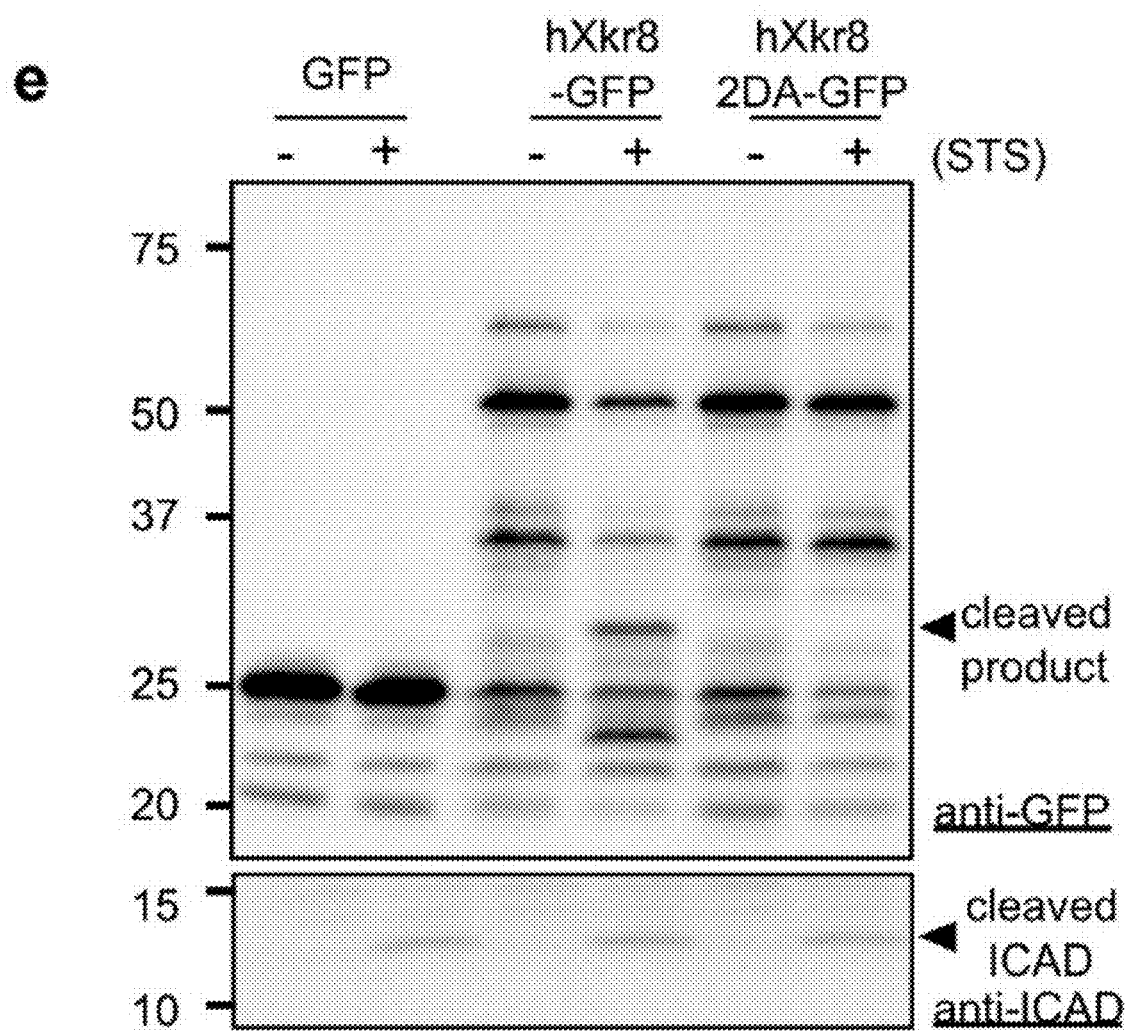

METHOD OF SCREENING MODULATOR OF XKR8

TECHNICAL FIELD

The present invention relates to a method of screening a modulator of Xkr8.

BACKGROUND

In eukaryotes, phospholipids that constitute plasma membrane are distributed asymmetrically in outer and inner leaflets. Phosphatidylserine (PtdSer) and phosphatidylethanolamine (PtdEtn) are present in the inner leaflets, while phosphatidylcholine (PtdCho) and sphingomyelin (SM) are mainly in the outer leaflet. The asymmetrical distribution of PtdSer and PtdEtn on the plasma membrane is maintained in an ATP-dependent manner by aminophospholipid translocase. The asymmetrical distribution of phospholipids is disrupted in various biological processes, and PtdSer exposed on the cell surface acts as a signaling molecule. For example, PtdSer exposed on apoptotic cells is an "eat me" signal for macrophages. On the activated platelets, PtdSer exposed on the cell surface activates blood coagulation factors and triggers the blood clotting.

PtdSer exposure to the cell surface is mediated by a phospholipid scramblase. However, the identity of the scramblase(s) has been unclear. Recently, TMEM16F has been identified as a $Ca^{2+}$-dependent phospholipid scramblase involved in the PtdSer exposure in activated platelets. However, TMEM16F-deficient cells exposed PtdSer in response to apoptotic stimuli as wild-type cells did, suggesting that TMEM16F has little involvement in apoptotic PtdSer exposure.

CITATION LIST

Patent Document

Patent Document 1: WO2012/029855

SUMMARY

Through the extensive research, the inventors identified Xkr8 as a protein involved in apoptotic PtdSer exposure and accomplished the disclosed invention.

The invention provides a method of screening a modulator of Xkr8, comprising the steps of:
(1) contacting Xkr8-expressing cells with a candidate of the modulator, and
(2) selecting the candidate when the candidate alters distribution of a phospholipid in plasma membrane of the cells.

According to the invention, a method of screening a modulator of Xkr8 is provided.

BRIEF DESCRIPTION OF DRAWINGS

FIG. 1c: Molecular cloning and characterization of Xkr8 (c). Real-time RT-PCR for mXkr8 in WR-Fas clones transformed with retrovirus carrying mXkr8 shRNA or scrambled shRNA.

FIG. 2c: No Xkr8 expression in PLB-985 or Raji cells (c). PLB-985 and Raji cells, and their hXkr8-transformants were treated with STS, UV, or FasL and stained with Cy5-Annexin V and Propidium iodide (PI). The active caspase 3-staining profiles for apoptotic cells were also shown together with those for growing cells (open area).

FIG. 3c: Epigenetic control of Xkr8 gene expression (c). PLB-985 cells were treated with DAC, and Xkr8 mRNA level was determined by real-time RT-PCR.

The caspase-recognition sites are boxed, and dibasic or diaromatic ER-transport signals are double-underlined.

Figure 5A:
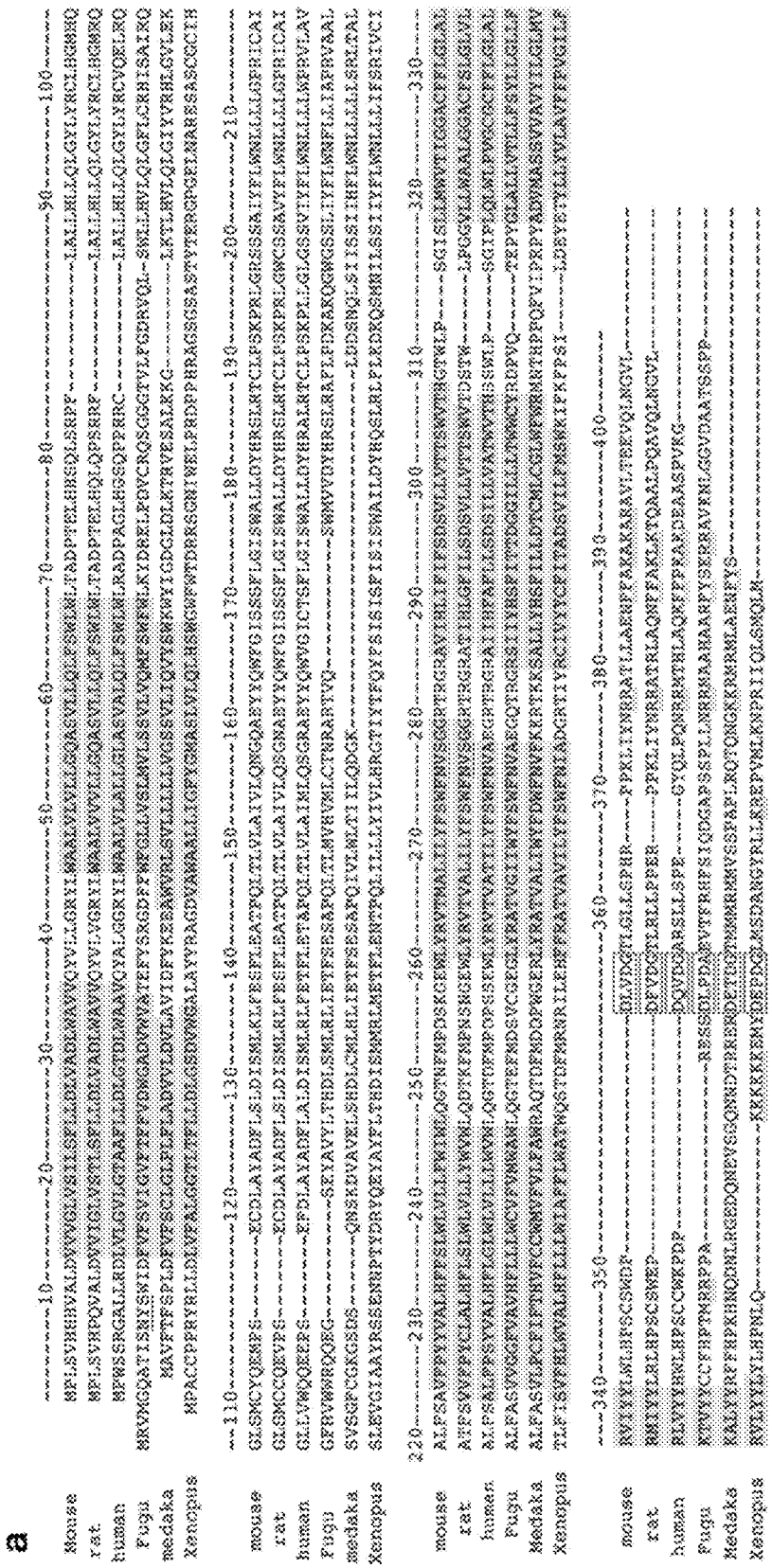
FIG. 5a: Activation of Xkr8 by caspase to elicit apoptotic PtdSer exposure (a). Amino acid sequences of Xkr8 of the listed species. Putative transmembrane regions are shaded.
Figure 5B:
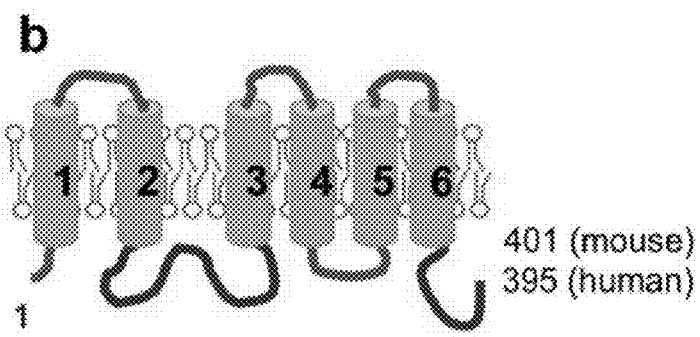

FIG. 5b: Activation of Xkr8 by caspase to elicit apoptotic PtdSer exposure (b). The Xkr8 structure is shown.

Figure 5C:
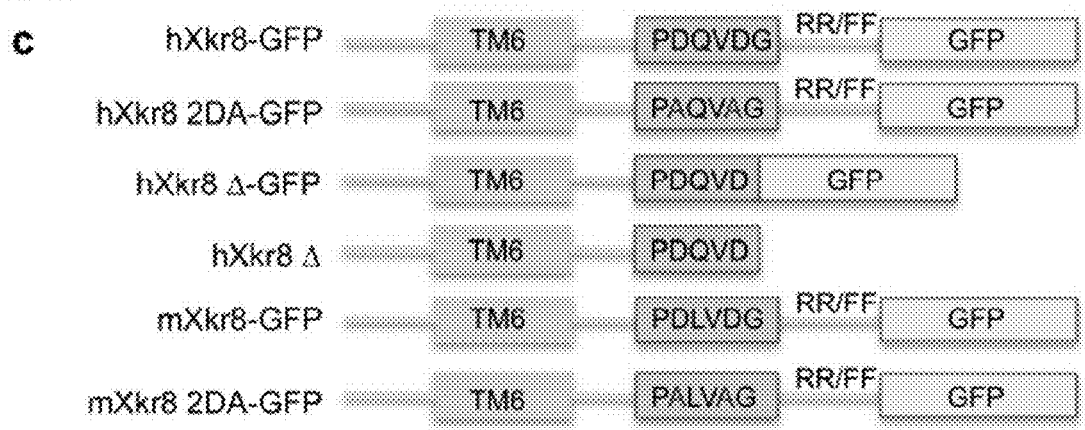

FIG. 5c: Activation of Xkr8 by caspase to elicit apoptotic PtdSer exposure (c). The wild-type, caspase-resistant (2DA) and truncation (D) mutant hXkr8 and mXkr8 fused to GFP are shown. TM, transmembrane; RR/FF, putative dibasic and diaromatic sequence for ER-exit.

Figure 5D:
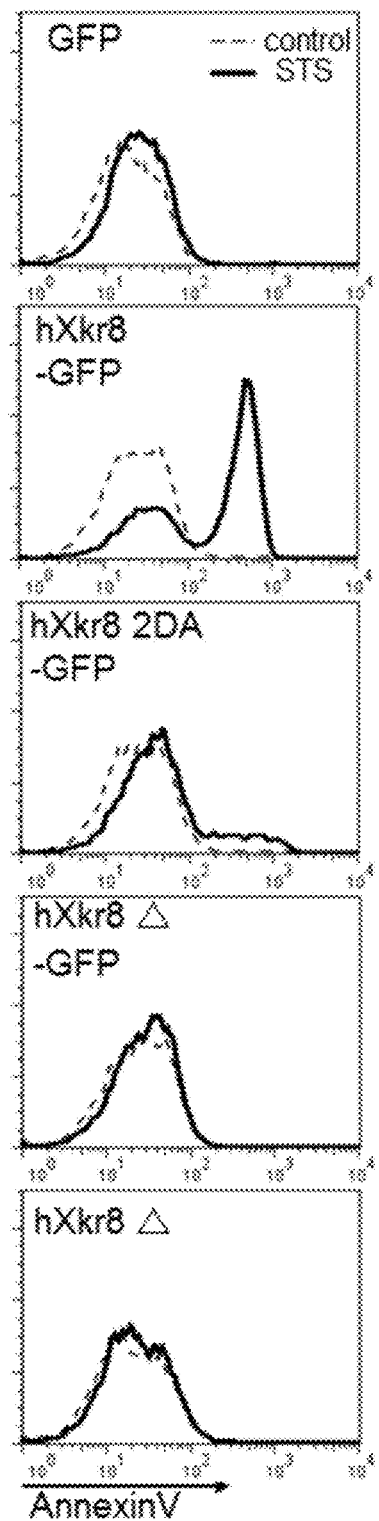

FIG. 5d: Activation of Xkr8 by caspase to elicit apoptotic PtdSer exposure (d). PLB-985 and its transformants expressing GFP, its fusion proteins with the wild-type or mutant hXkr8, were exposed to STS, and stained with Cy5-Annexin V.

FIG. 5e: Activation of Xkr8 by caspase to elicit apoptotic PtdSer exposure (e). Cell lysates of FIG. 5d were analyzed with anti-GFP and anti-ICAD FIG. 5f: Activation of Xkr8 by caspase to elicit apoptotic PtdSer exposure (f). WR-Fas and its transformants expressing GFP, mXkr8-GFP or mXkr8 2DA-GFP were treated with FasL. Cell lysates were analyzed by Western blotting with anti-GFP.

Figure 5F:
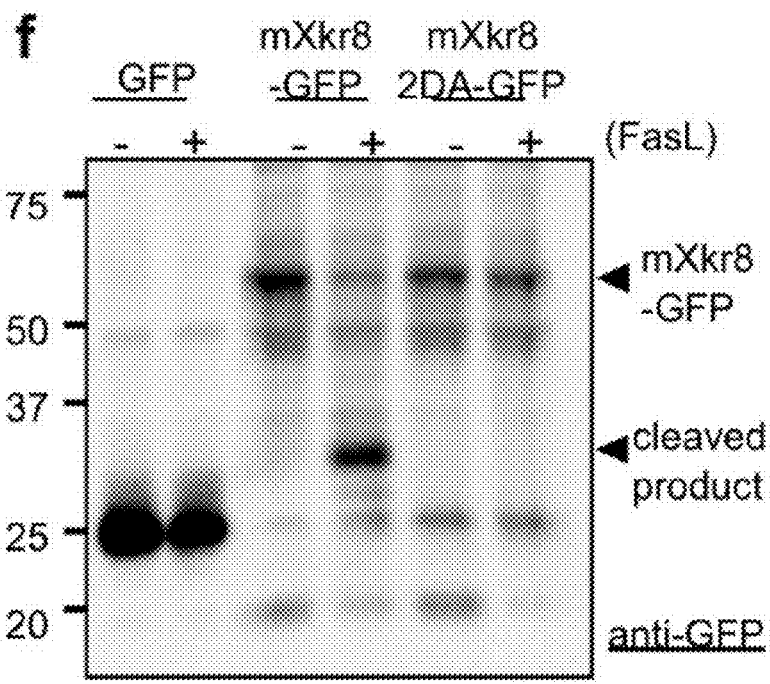
Figure 5G:
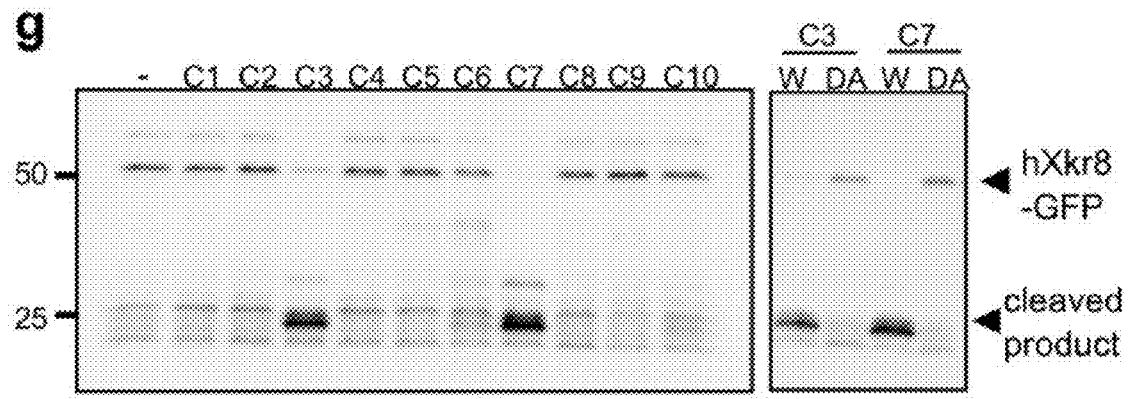

FIG. 5g: Activation of Xkr8 by caspase to elicit apoptotic PtdSer exposure (g). The membrane fraction from PLB-985 transformants expressing hXkr8-GFP (W) or hXkr8 2DA-GFP (DA) were incubated with the indicated human recombinant caspases (C1 to C10, caspase 1 to caspase 10), and analyzed by Western blotting with anti-GFP.

Figure 5H:
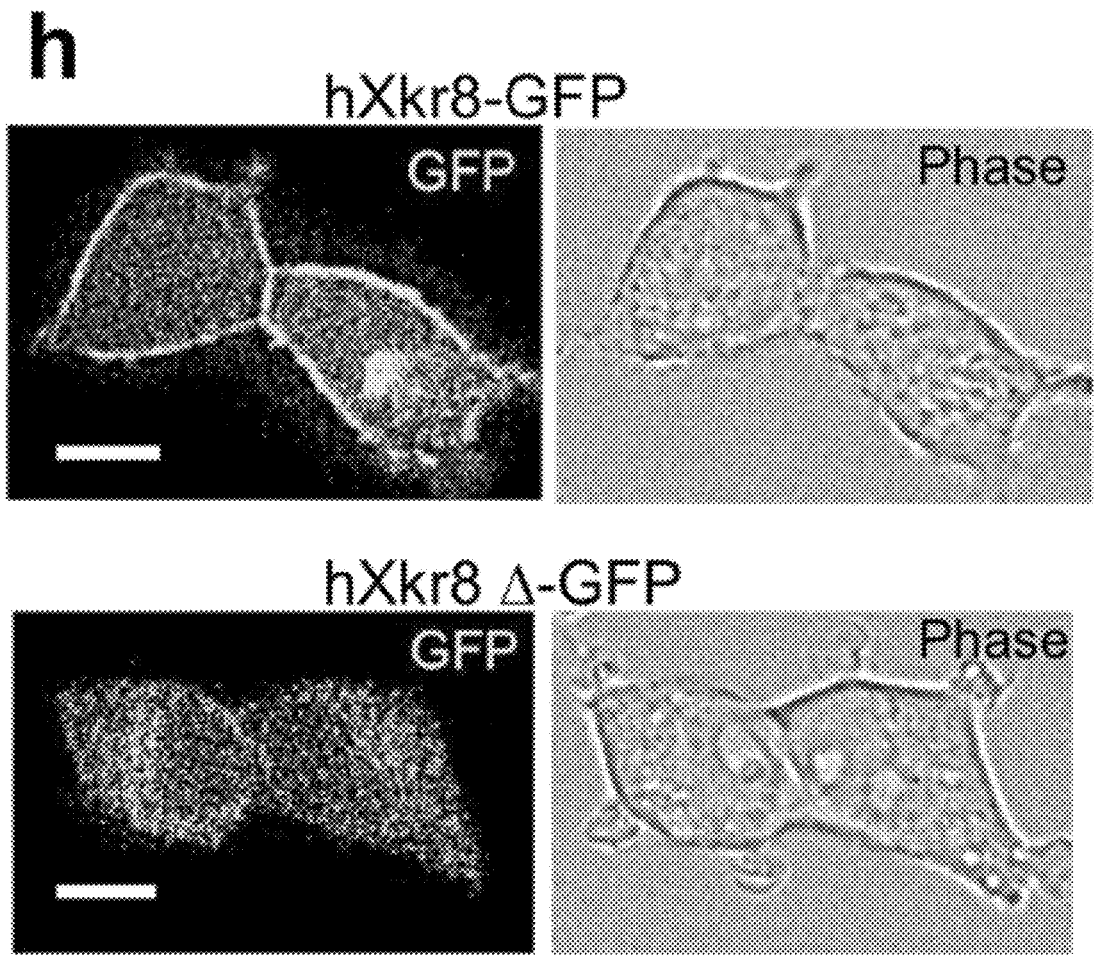

FIG. 5h: Activation of Xkr8 by caspase to elicit apoptotic PtdSer exposure (h). 293T cell transformants expressing hXkr8-GFP or hXkr8D-GFP were observed by fluorescence microscopy. Scale bar, 10 μm.

Figure 6A:
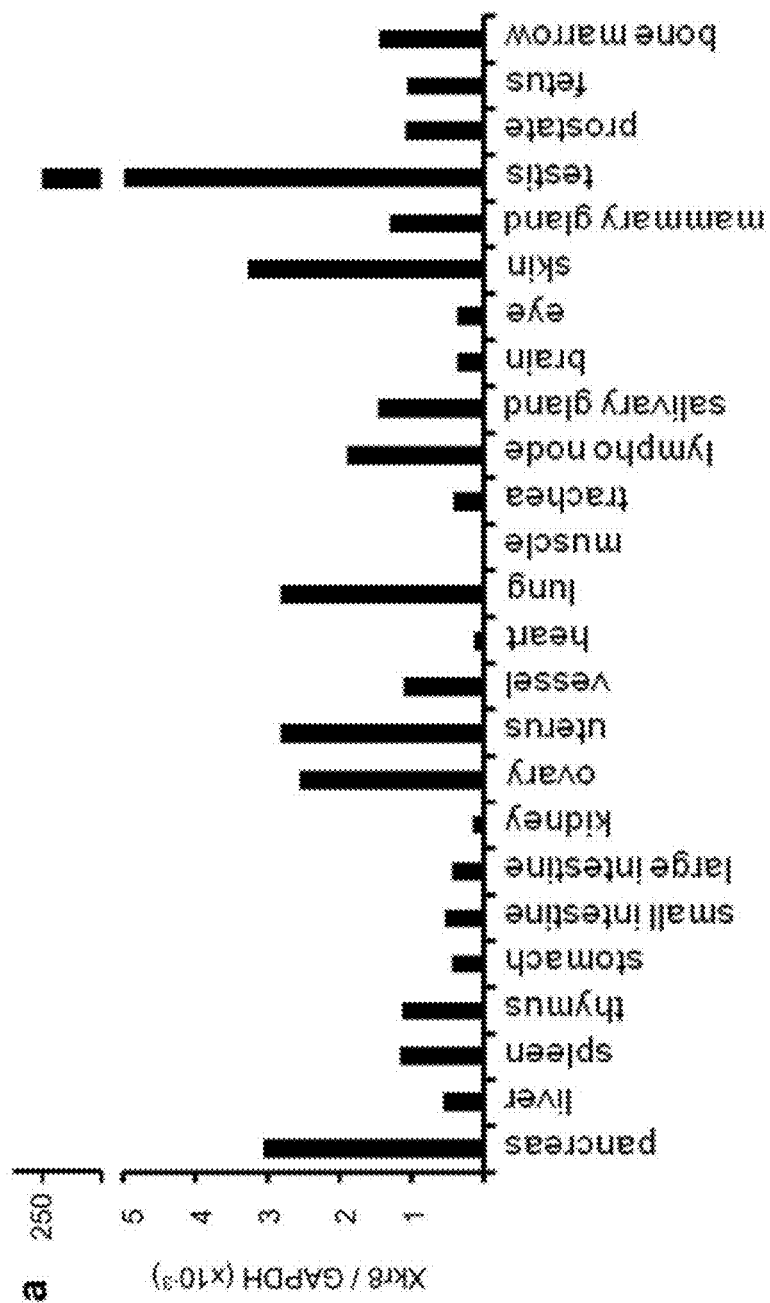

FIG. 6a: Establishment of mouse $Xkr8^{-/-}$ foetal thymocyte cell lines (a). The Xkr8 mRNA level in the indicated mouse tissues was determined by real-time RT-PCR, and expressed relative to Gapdh mRNA.

Figure 6B:
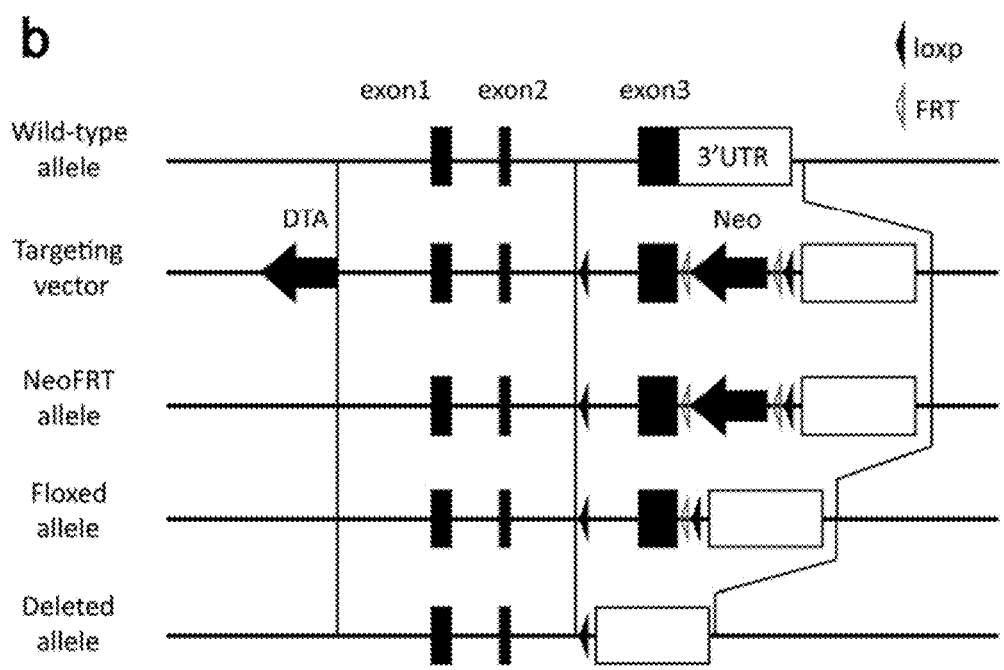

FIG. 6b: Establishment of mouse $Xkr8^{-/-}$ foetal thymocyte cell lines (b). Structures of the wild-type, floxed and deleted alleles of the mXkr8 chromosomal gene and its targeting vector are shown.

Figure 6C:
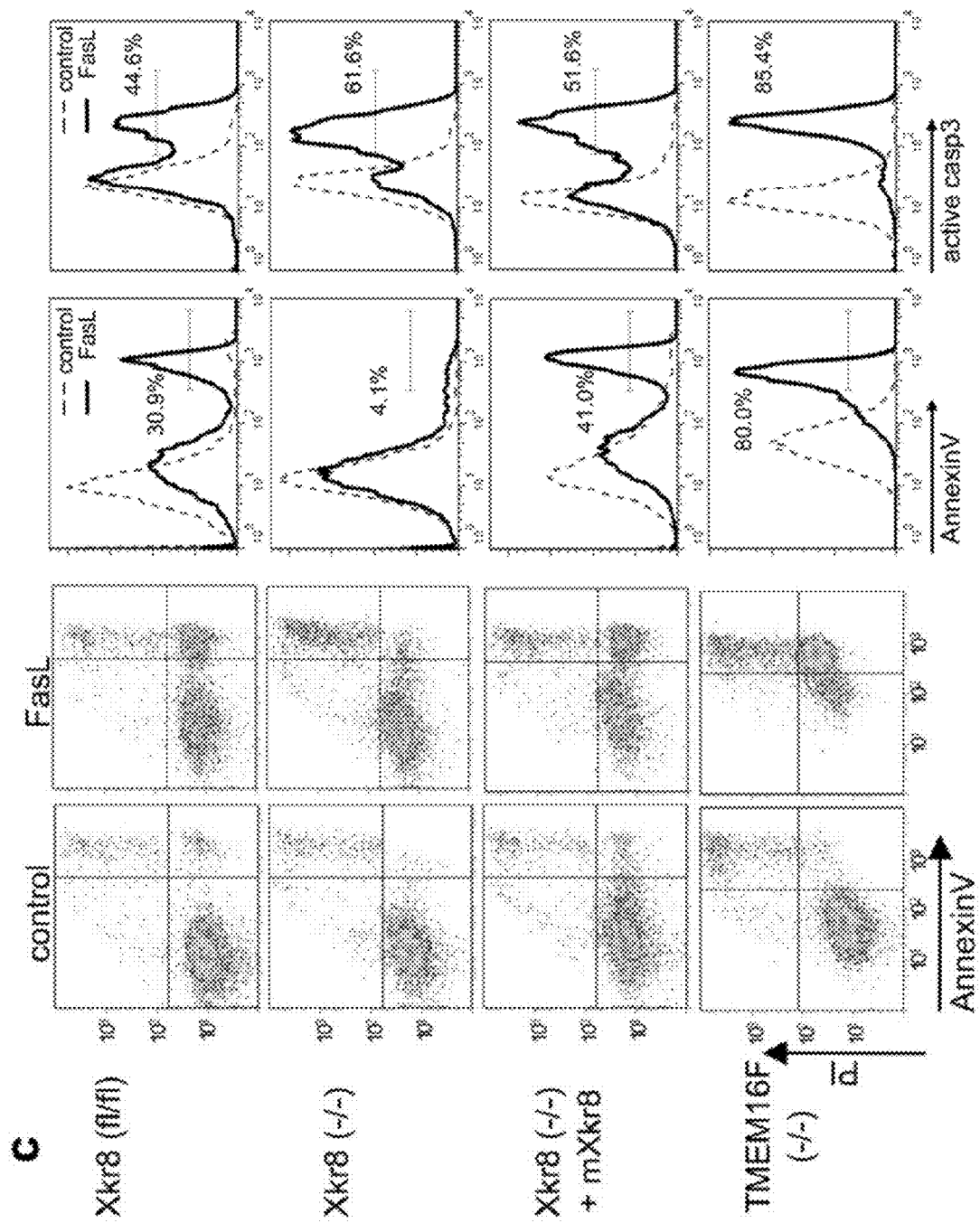

FIG. 6c: Establishment of mouse $Xkr8^{-/-}$ foetal thymocyte cell lines (c). The $Xkr8^{flox/flox}$, $Xkr8^{-/-}$, and Xkr8-transformed $Xkr8^{-/-}$ and $TMEM16F^{-/-}$ IFET cells were treated with FasL and stained with Cy5-Annexin V and PI, or anti-active caspase 3.

Figure 6D:
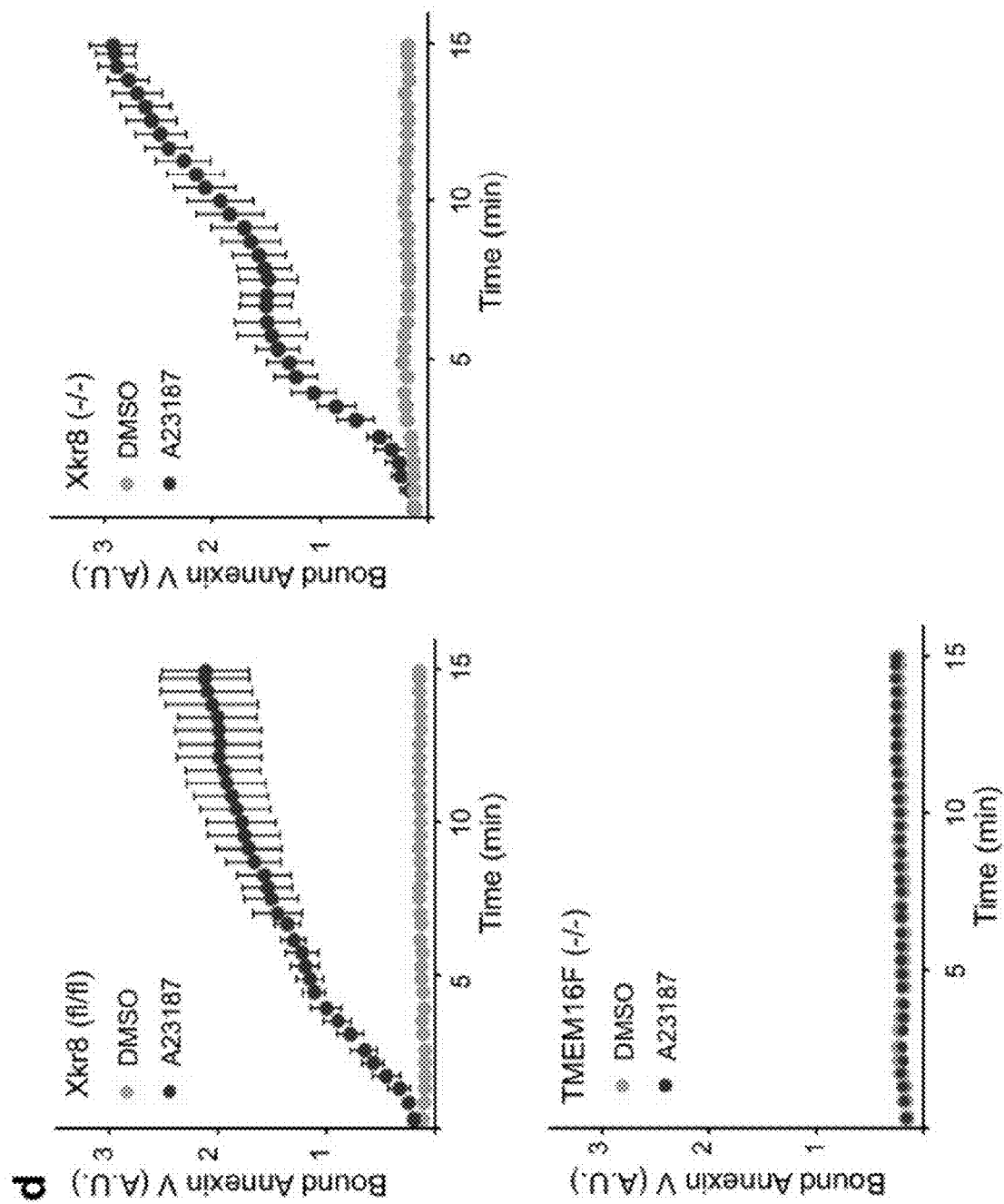

FIG. 6d: Establishment of mouse $Xkr8^{-/-}$ foetal thymocyte cell lines (d). Wild-type, $Xkr8^{-/-}$ and $TMEM16F^{-/-}$ IFET cells were treated with A23187 in the presence of Cy5-Annexin V, and Annexin V binding to the cells was monitored by flow cytometry.

Figure 7A:
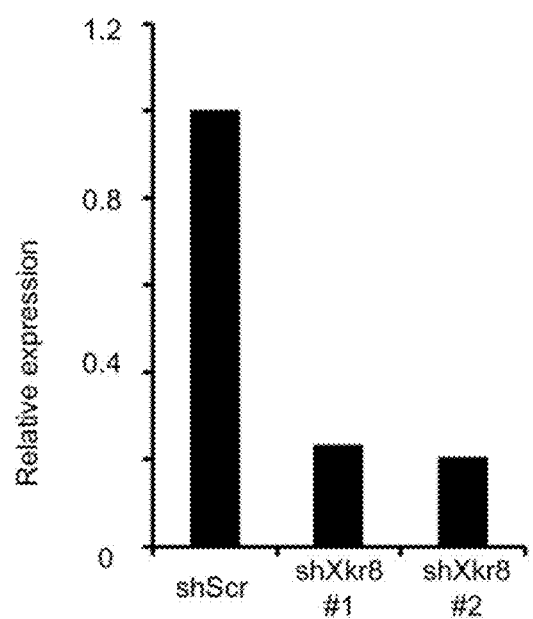

FIG. 7a: Effect of knock-down of Xkr8 on the FasL-induced PtdSer exposure in Ba/F3 cells (a). Real-time PCR for mXkr8 in Ba/F3-Fas clones transformed with retrovirus carrying mXkr8 shRNA or scrambled shRNA.

Figure 7B:
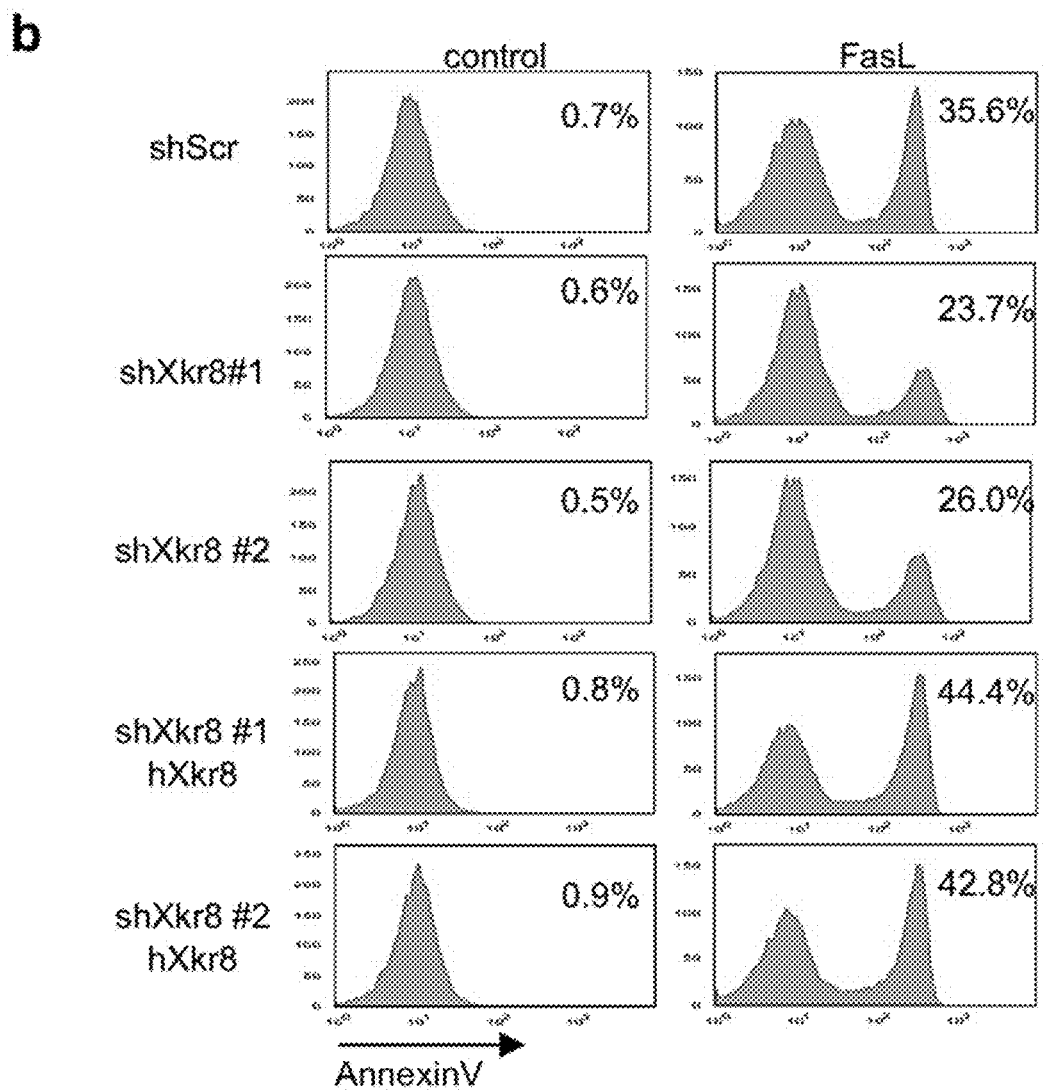

FIG. 7b: Effect of knock-down of Xkr8 on the FasL-induced PtdSer exposure in Ba/F3 cells (b). Ba/Fas-Fas and its mXkr8 shRNA-expressing transformants, two clones each, were treated with FasL and stained with Cy5-Annexin V.

Figure 8:
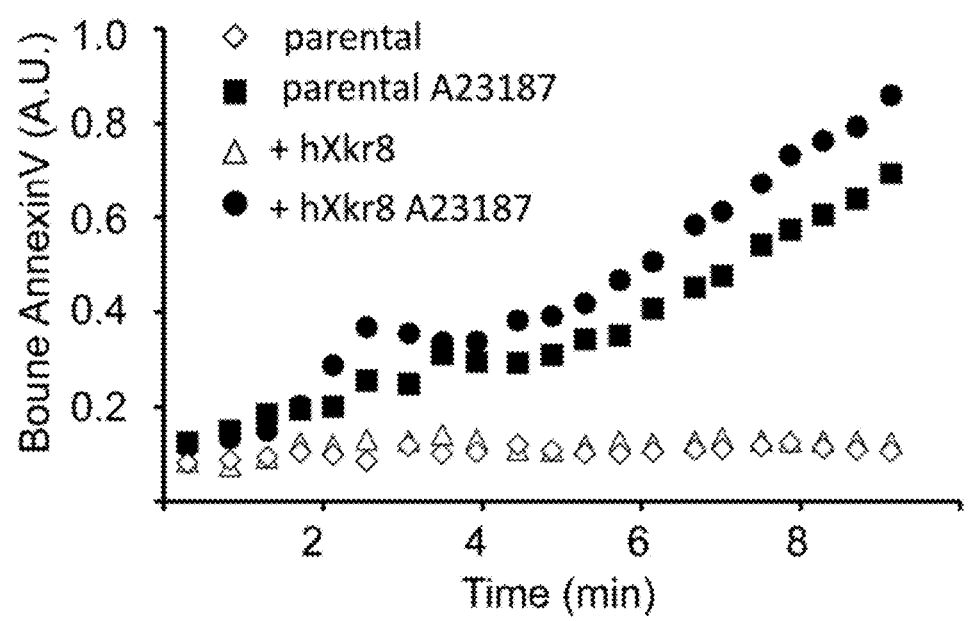

FIG. 8: Effect of hXkr8 on Ca-dependent PdtSer exposure. PLB-985 and its hXkr8 transformant were treated at 20° C. with 1.0 μM A23187 and Cy5-labeled Annexin V, and Annexin V-binding to the cells was monitored by flow cytometry for 10 min.

DESCRIPTION OF EMBODIMENTS

Xkr8 is a membrane protein having 6 transmembrane regions. The nucleic acid sequences of human and mouse Xkr8 are disclosed under GenBank NM_018053 and GenBank NM_201368. The amino acid sequences of mouse, rat, human, Fugu, medaka, and *Xenopus* Xkr8 (SEQ ID NOS: 1-6) are shown in FIG. 5a.

"A candidate of a modulator of Xkr8" may be a natural or synthetic product. Examples of the candidate of a modulator of Xkr8 include low-molecular compounds, proteins, nucleic acid molecules, peptides, antibodies, or cell extract or culture supernatant of microorganisms, plants or animals. The candidate may be provided in a form of a library, such as a library of low-molecular compounds, peptides, or antibodies.

As used herein, "Xkr8-expressing cells" includes cells that express Xkr8 in nature from the genome, and cells that express Xkr8 from a gene encoding Xkr8 introduced into the cells. The cells may be derived from, but not limited to, human, monkey, mouse, or rabbit. For example, human HeLa, human EBV (Epstein Barr Virus)-transformed B cell line, mouse MEF (embryonal fibroblasts), and mouse pro B cell line Ba/F3 may be used in the invention. The gene encoding Xkr8 may be introduced into cells to prepare Xkr8-expressing cells by methods well known in the art (Molecular Cloning: A Laboratory Manual (Fourth Edition), Cold Spring Harbor Laboratory Press).

The modulator of Xkr8 includes both "a modulator enhancing a function of Xkr8" and "a modulator suppressing a function of Xkr8". As used herein, "enhancing (or suppressing) a function of Xkr8" means potentiating (or inhibiting) the function of Xkr8 as a lipid scramblase in cells or animals. The modulator of Xkr8 may be an agent directly or indirectly affecting the function of Xkr8, or an agent increasing or decreasing expression of Xkr8. The agent increasing or decreasing expression of Xkr8 includes an agent increasing or decreasing mRNA expression from a gene encoding Xkr8, and an agent increasing or decreasing Xkr8 protein expression. Therefore, the modulator of Xkr8 includes an agent affecting a regulatory sequence of the gene encoding Xkr8, such as a promoter or enhancer, and also includes an antisense oligonucleotide (DNA or RNA), siRNA, miRNA, and lybozyme prepared according to the sequence of the gene encoding Xkr8. Since Xkr8 is activated by cleavage with caspase, the modulator of Xkr8 includes an agent increasing or decreasing the cleavage of Xkr8 with caspase.

In the method of the invention, the enzymatic activity of Xkr8 as a phospholipid scramblase is measured. The phospholipid is selected from the group consisting of phosphatidylserine (PtdSer), phosphatidylethanolamine (PtdEtn), phosphatidylcholine (PtdCho), and sphingomyelin (SM). Under the normal condition, PtdSer and PtdEtn are distributed in the inner leaflet of plasma membrane and PtdCho and SM are distributed in the outer leaflet of plasma membrane. Xkr8 moves PtdSer and PtdEtn to the outer leaflet of plasma membrane (i.e., exposes PtdSer and PtdEtn) and moves PtdCho and SM to the inner leaflet of plasma membrane (i.e., internalizes PtdCho and SM). The enzymatic activity of Xkr8 may be measured by determination of the lipid distribution in plasma membrane.

A candidate is selected as a modulator enhancing a function of Xkr8 when the candidate increases distribution of PtdSer and PtdEtn in the outer leaflet of plasma membrane (i.e., increases exposure of PtdSer and PtdEtn) compared to the control. In contrast, a candidate is selected as a modulator suppressing a function of Xkr8 when the candidate decreases distribution of PtdSer and PtdEtn in the outer leaflet of plasma membrane (i.e., decreases exposure of PtdSer and PtdEtn) to the control. Also, a candidate is selected as a modulator enhancing a function of Xkr8 when the candidate increases distribution of PtdCho and SM in the inner leaflet of plasma membrane (i.e., increases internalization of PtdCho and SM) compared to the control. In contrast, a candidate is selected as a modulator suppressing a function of Xkr8 when the candidate decreases distribution of PtdCho and SM in the inner leaflet of plasma membrane (i.e., decreases internalization of PtdCho and SM) compared to the control.

As used herein, "control" means distribution of the same lipid in the same leaflet (outer or inner leaflet) in Xkr8-expressing cells in the absence of the candidate of the modulator.

In the step of contacting Xkr8-expressing cells with a candidate of a modulator of Xkr8 (step (1)), typically, the candidate is added to the culture medium of the Xkr8-expressing cells in the presence of an apoptotic stimulus. Examples of the apoptotic stimulus include an apoptotic molecule, such as Fas and staurosporine, and UV irradiation. The apoptotic stimulus may be added to the culture medium before or after the addition of the candidate to the culture medium, or may be added simultaneously with the candidate.

Distribution of PtdSer in plasma membrane may be determined by detection of the binding between PtdSer exposed on the cell surface and an agent having the property to bind to PtdSer, such as AnnexinV or MFG-E8 (also called as lactadherin). For example, after Xkr8-expressing cells are treated with fluorescently-labelled AnnexinV, the amount of AnnexinV bound to the cell surface is measured.

Distribution of PtdSer in plasma membrane also may be determined based on blood-clotting reaction. For example, in the presence of an apoptotic stimulus, Xkr8-expressing cells are mixed with a candidate of the modulator and agents required for blood coagulation such as factor Xa, factor Va, and prothrombin, and then production of thrombin is measured. Alternatively, fibrinogen may be further added to the cell culture to measure production of fibrin.

Distribution of PtdEtn in plasma membrane may be determined by detection of the binding between PtdEtn exposed on the cell surface and an agent having the property to bind to PtdEtn, such as a PtdEtn-binding peptide, R009-0198. For example, after Xkr8-expressing cells are treated with biotin-labelled R009-0198 and stained with fluorescently-labeled streptavidin, the amount of R009-0198 bound to the cell surface is measured.

Distribution of PtdCho and SM in plasma membrane may be determined with a fluorescently-labeled lipid. As a fluorescent label, NBD and TopFluor may be used. For example, a fluorescently-labeled lipid is added to the culture medium such that the fluorescently-labeled lipid is incorporated into the outer leaflet of plasma membrane of Xkr8-expressing cells. When Xkr8 functions as a lipid scramblase, the fluorescently-labeled lipid is moved to the inner leaflet of plasma membrane (i. e., internalized). Therefore, Xkr8-expressing cells may be treated with a candidate of the modulator together with an apoptotic stimulus in the presence of a fluorescently-labeled lipid such as NBD-PC or NBD-SM. The cells are then treated with BSA such that the fluorescently-labeled lipid unincorporated into the cells is removed. Finally, the fluorescently-labeled lipid incorporated into the cells is measured by a flow cytometry.

Xkr8 is involved in the PtdSer exposure in apoptotic cells. Therefore, the invention is useful to develop therapeutic agents for apoptotic diseases. Examples of the apoptotic diseases include autoimmune diseases, cancers, AIDS, and brain diseases such as Alzheimer's disease.

The invention is further illustrated by, but not limited to, the following examples.

EXAMPLE 1

1. Methods
(1) Cell Lines, Recombinant Proteins, Antibodies, and Materials

Mouse interleukin (IL-3)-dependent Ba/F3 cells[50] were maintained in RPMI containing 10% foetal calf serum (FCS, Gibco), 45 units/ml mouse IL-3, and 50 µM β-mercaptoethanol. Human PLB-985[51], Jurkat (ATCC TIB152), Namalwa (ATCC CRL-1432) , and Raji (ATCC CCL-86) cells were grown in RPMI1640 containing 10% FCS and 50 µM β-mercaptoethanol. Plat-E packaging cells[52] were grown in DMEM containing 10% FCS. Recombinant mouse IL-3[53], and human FasL[54] were prepared as described. Rabbit anti-activated caspase 3 mAb was from Cell Signaling. Mouse anti-human ICAD mAb was from Medical & Biological Laboratories (MBL), and Alexa 488- and Alexa 568-labeled goat anti-rabbit IgG were from Invitrogen. Staurosporine was provided by Kyowa Hakko Kirin.

(2) Construction of a cDNA Library, and Identification of Xkr8

Using poly(A) RNA from Ba/F3-PS19 cells, double-stranded cDNA was synthesized with random hexamers as primers, and a BstXI adaptor was attached as described[55]. DNA fragments of 1.0 to 2.5 kb in length were size-fractionated by electrophoresis through a 1% agarose gel, and ligated into a Bst XI-digested pMXs vector[56]. Approximately $1.3 \times 10^6$ clones were produced by transforming *E. coli* DH10B cells (ElectroMax DH10B; Invitrogen) by electroporation. Using plasmid DNA from the cDNA library, retrovirus was produced in Plat-E cells, concentrated by centrifugation, and used to infect Ba/F3 cells as described[55]. Cells treated with A23187 were stained on ice for 15 min with Cy5-Annexin V (Biovision) and for 2 min with 5 µg/ml Propidium Iodide (PI), and sorted with FACSAria (BD Biosciences). The cDNA integrated into the retroviral vector was identified by PCR with the DNA from Ba/F3 cell transformants as described[55].

(3) Expression Plasmids for Mouse and Human Xkr8, and their Mutants

The full-length coding sequences for mXkr8 (GenBank NM_201368) and hXkr8 (GenBank NM_018053) were prepared by RT-PCR from Ba/F3 cells and Namalwa cells, respectively. Primers used were as follows (in each primer, the Bam HI or Eco RI recognition sequence is underlined):

```
                                          (SEQ ID NO; 7)
mXkr8: 5'-ATATGGATCCATCATGCCTCTGTCCGTGCACCA-3'
and (SEQ ID NO; 8)
5'-ATATGAATTCGAGGACTCCATTCAGCTGCA-3'

(SEQ ID NO; 9)
hXkr8: 5'-ATATGGATCCGCCATGCCCTGGTCGTCCCGCGG-3'
and (SEQ ID NO; 10)
5'-ATATGAATTCTCCCTTCACTGGCGAAGCAG-3'.
```

The pMXs puro c-GFP was constructed by inserting the GFP sequence between the Eco RI and Xho I sites of pMXs puro. The Xkr8 cDNAs were then inserted into the Bam HI/Eco RI site of pMXs puro c-FLAG[55] or of pMXs puro c-GFP to express proteins tagged with FLAG or GFP at the C-terminus. To generate the D351A/D354A (2DA) mutants of mXkr8 and the D352A/D355A (2DA) mutants of hXkr8, the mouse and human Xkr8 cDNAs were mutated by recombinant PCR[57] using 30-nucleotide primers carrying the mutated nucleotides:

```
                                              (SEQ ID NO: 11)
mXkr8 2DA: 5'-GGGACCCTGCCCTCGTGGCTGGGACCCTAG-3'
and
                                              (SEQ ID NO: 12)
5'-CTAGGGTCCCAGCCACGAGGGCAGGGTCCC-3'

(SEQ ID NO: 13)
hXkr8 2DA: 5'-AAGCCCGACCCTGCCCAGGTAGCCGGGGCC-3'
and
                                              (SEQ ID NO: 14)
5'-GGCCCCGGCTACCTGGGCAGGGTCGGGCTT-3'.
```

To construct the C-terminal deletion mutants of hXkr8, PCR was performed using a mutant reverse primer: 5'CGA-GATCTGAATTCTCAGTCTACCTGGTCAGGGTCGG-3' (SEQ ID NO: 15) (the Eco RI recognition sequence is underlined), and the product was inserted into a pMXs puro vector.

(4) shRNA

Four shRNA expression plasmids for mXkr8 in a pRS shRNA vector carrying the puromycin-resistance gene were purchased from OriGene. Among the four sequences, the best target sequence for shRNA was 5'-GAATCTGTGC-CATCGCCTTGTTCTCAGCT-3' (SEQ ID NO: 16). The scrambled shRNA in pRS was also from OriGene. Ba/F3 cells were infected with retrovirus containing the shRNA, while WR19L were transfected by electroporation. Stable transformants were selected by culturing in medium with 1.0 μg/ml puromycin, and subjected to cloning by limited dilution. The Xkr8 mRNA was quantified by real-time RT-PCR.

(5) Establishment of Xkr8 Conditional Knock-Out Mice

Xkr8 conditionally targeted mice were generated as a custom order by Unitech. In brief, a neo-loxP cassette carrying the phosphoglycerate kinase (PGK) promoter-driven neomycin-resistance (neo) gene flanked by FRT sequences was inserted into intron 3 of the Xkr8 gene. A 1.0-kb DNA fragment containing exon 3 was replaced with a fragment carrying the corresponding sequence and a locus of crossing over in the P1 (loxP) sequence. The diphtheria toxin A-fragment (DT-A) driven by the thymidine kinase (tk) promoter was inserted at the 5' end of the vector. Mouse Bruce-4h embryonic stem (ES) cells[58] were transfected with the targeting vector, and the G418-resistant clones were screened for homologous recombination by PCR. Positive clones were injected into blastocysts to generate $Xkr8^{+/NeoFRT}$ mice. The $Xkr8^{+/NeoFRT}$ mice were crossed with transgenic mice carrying the cytomegalovirus enhancer-chicken β-actin hybrid promoter (CAG)-driven flippase variant (FLPe) gene (CAG-FLPe)[59], and the resulting mice were backcrossed to C57BL/6 to generate $Xkr8^{+/flox}$ mice. All the mice were housed in a specific pathogen-free facility (SPF, a facility which is free of specific microorganisms or parasites) at Kyoto University, and all animal experiments were carried out in accordance with protocols approved by Kyoto University.

(6) Establishment of Foetal Thymocyte Cell Lines

An immortalized foetal thymocyte cell line (IFET) was established by immortalizing foetal thymocytes with H-ras$^{V12}$ and c-myc as described[60,61]. In brief, the $Xkr8^{+/flox}$ mice were intercrossed, and foetal thymocytes were obtained on embryonic day (E) 14.5. Retrovirus carrying the genes for H-ras$^{V12}$ and c-myc was produced in Plat-E cells with the pCX4 vector[62], and bound to RetroNectin-coated plates (Takara Bio) by centrifugation at 2,000×g for 2-3 h at room temperature. The thymocytes were attached to the retrovirus-coated plate by centrifugation at 400×g for 5 min, and cultured in DMEM containing 10% FCS, 1× non-essential amino acids, 10 mM Hepes-NaOH buffer (pH 7.4), 50 μM β-mercaptoethanol, 5 ng/ml mouse IL-7[63] (Pepro-Tech), and GlutaMax™ (Gibco). The resultant IFET cells were infected with Adeno-Cre (Adenovirus Cre/loxP, Takara Bio), and subjected to cloning by limited dilution. Clones carrying the Xkr8$^{-/-}$ allele were selected by PCR with the following primers (wild-type-specific sense primer: 5'-CT-CATTGCTGATGTGGGTGACAATA-3' (SEQ ID NO: 17); mutant-specific sense primer: 5'-AGGCTTTTCTC-TACTTTTGATGGAG-3' (SEQ ID NO: 18); and common anti-sense primer, 5'-CATTATCTTCCTCACTGGCT-GAATC-3' (SEQ ID NO: 19)).

(7) Transformation of Human and Mouse Cells

Retroviruses carrying mouse and human Xkr8 cDNA were produced by introducing the pMX-puro vector into Plat-E cells, concentrated by centrifugation, and used to infect Ba/F3 and Xkr8$^{-/-}$ IFET cells. Stable transformants were selected in medium containing puromycin (1.0 μg/ml and 2.0 μg/ml for Ba/F3 and IFET cells, respectively), and the expression of the recombinant protein was confirmed by Western blotting with an anti-Flag (Clone M2, Sigma) or anti-GFP (Clone JL8, Clontech). Mouse Fas cDNA[64] was introduced into IFET cells by retrovirus-mediated transformation, and its expression was confirmed by flow cytometry with the anti-mouse Fas mAb (Jo2)[65]. Human PLB-985 and mouse WR19L cells were transformed by retrovirus infection with amphotropic retrovirus envelope or VSVγ envelope. In brief, retrovirus was generated by co-transfecting 293T cells with the pMXs retrovirus vector, pGP (Takara Bio) for Gag and pol-fusion protein, and pE-ampho (Takara Bio) or pCMV-VSV-G-RSV-Rev (provided by Dr. H. Miyoshi, Riken). The virus particles in the culture supernatant were concentrated by centrifugation and used to transform cell lines. To express Xkr8-GFP in 293T cells, 293T cells were transfected with pMXs puroXkr8-GFP by lipofection with Fugene 6 (Promega). Stable transformants were selected in medium containing 1.0 μg/ml puromycin.

(8) Induction of Apoptosis, Treatment with $Ca^{2+}$-Ionophore, and Flow Cytometry Apoptosis was induced by treating cells with FasL or staurosporine, or exposing them to UV. In brief, $5\times10^5$ cells in 500 μl of culture medium were incubated at 37° C. with 10-400 units/ml hFasL for 1.2-2.0 h or with 10 μM staurosporine for 1.5-4.0 h. For UV exposure, $1\times10^6$ cells in 2 ml of PBS were exposed to 500-2000 J/m UV radiation (254 nm) in a StrataLinker UV oven (Stratagene), and incubated at 37° C. for 1.5-2.0 h in 4 ml of RPMI1640 containing 10% FCS. To monitor $Ca^{2+}$-ionophore-induced PtdSer exposure, cells ($5\times10^5$ cells) in 500 μl of Annexin V staining buffer (10 mM Hepes-NaOH buffer [pH7.4] containing 140 mM NaCl and 2.5 mM $CaCl_2$) were incubated at 20° C. for 3 min, treated with 3.0-10 μM A23187, and analyzed with FAC-SAria at 20° C.

To detect active caspase 3 in cells, cells ($1\times10^6$ cells) were fixed by incubation at 37° C. for 10 min in PBS containing 1% paraformaldehyde (PFA). After washing with chilled PBS containing 0.5% BSA, the cells were permeabilized by overnight incubation at −20° C. in 90% methanol. The cells were then incubated with 200-fold-diluted rabbit anti-active caspase 3 at room temperature for 30 min, followed by incubation for 30 min with 1,000-fold-diluted Alexa 488- or Alexa 568-labeled goat anti-rabbit IgG. After washing with PBS containing 0.5% BSA, the cells were filtered into FACS tube and analyzed by FACSAria.

(9) Assay for Phospholipid Scrambling Activity

To detect PtdSer and PtdEtn exposed on the cell surface, cells were stained on ice for 15 min with 2500-5000-fold diluted Cy5-Annexin V (Biovision) or 800-fold diluted-biotin-Ro09-0198[66] followed by 1.0 µg/ml APC-streptavidin in Annexin V staining buffer in the presence of 5 µg/ml propidium iodide (PI), and analyzed by FACSAria or FACSCalibur (BD Biosciences). To assay the internalization of PtdCho and SM, 1×10⁶ cells in 0.5 ml of HBSS containing 1 mM $CaCl_2$ (HBSS-Ca) were incubated on ice for 7 min. An equal volume of 200 nM 1-oleoyl-2-{6-[(7-nitro-2-1,3-benzoxadiazol-4-yl)amino]hexanoyl}-sn-glycero-3-phosphocholine (NBD-PC) (Avanti Polar Lipids), or N-[6-[(7-nitro-2-1,3-benzoxadiazol-4-yl)amino]hexanoyl]-sphingosine-1-phosphocholine (NBD-SM) (Avanti Polar Lipids) in HBSS-Ca was added, and incubated at 20° C. Aliquots (150 µl) were mixed with 150 µl HBSS containing 5 µg/ml fatty-acid free BSA (Sigma-Aldrich) and 500 nM Sytoxblue (Molecular Probes), and analyzed by FACSAria.

(10) Treatment with 5-aza-2'-deoxycytidine, and bisulfite genomic Sequencing

To treat human PLB-985 cells with 5-aza-2'-deoxycytidine (DAC, Sigma-Aldrich), 1.0×10⁶ cells in 10 ml of RPMI containing 10% FCS were incubated with 0.5 µM DAC for up to 7 days. Since DAC is an unstable compound, the medium containing DAC was changed every 24 hours. After DAC treatment, the cells were divided into three portions: one portion for FACS to analyze the PtdSer exposure, one for real-time RT-PCR for Xkr8 gene expression, and one for the methylation-specific PCR analysis[67]. For the bisulfite genomic sequencing, the DNA was modified with bisulfite using a kit (MethyEasy Xceed, Human Genetic Signatures). In brief, 3 µg DNA was denatured by incubation at 37° C. for 15 min in 0.3 M NaOH, and treated with sodium bisulfite according to the protocol provided by the supplier except that the incubation time was changed to 90 min. The modified DNA was denatured at 95° C. for 20 min, and amplified by PCR using primers specific for the treated DNA (TTAGGGATTAGAATGTGTTT (SEQ ID NO; 20) and CCTATACAAATAACCCAACT (SEQ ID NO; 21)). PCR was carried out with EpiTaq HS polymerase (Takara Bio) for 7-40 cycles, and the product was cloned in a pGEM-Teasy vector for sequencing.

(11) Real-Time RT-PCR

Total RNA from human and mouse cell lines and various mouse tissues was reverse-transcribed using Superscript III reverse-transcriptase (Invitrogen) or the High Capacity RNA-to-cDNA™ kit (Applied Biosystems). Aliquots of the products were amplified in a reaction mixture containing LightCycler™ 480 SYBR Green I Master (Roche Diagnostics). The primers for real-time RT-PCR were:

```
                                      (SEQ ID NO; 22)
mXkr8: 5'-GCGACGCCACAGCTCACACT-3'
and (SEQ ID NO; 23)
5'-CCCCAGCAGCAGCAGGTTCC-3'

(SEQ ID NO; 24)
mGapdh: 5'-AGCAGGCATCTGAGGGCCCA-3'
and (SEQ ID NO; 25)
5'-GAGAGCAATGCCAGCCCCGG-3'
```

```
                                      (SEQ ID NO; 26)
hXkr8: 5'-AGGCCGGGCCATCATCCACT-3'
and (SEQ ID NO; 27)
5'-TGCGCCTGTTCTGAGGCAGC-3',
and (SEQ ID NO; 28)
human β-actin: 5'-GCATCCTCACCCTGAAGTAC-3'
and (SEQ ID NO; 29)
5'-CTTAATGTCACGCACGATTTC-3'.
```

The specific mRNA was quantified at the point where the LightCycler System detected the upstroke of the exponential phase of PCR accumulation with the respective linearized plasmid DNA as reference.

(12) Treating the Cell Lysates with Caspase

Membrane fractions were prepared from PLB-985 cell transformants expressing hXkr8-GFP or hXkr8 2DA-GFP as described previously[53]. Membranes were then solubilized by suspending in lysis buffer (20 mM Tris-HCl [pH 7.2], 140 mM NaCl, 1% Triton X-100, 10% glycerol, and 1 mM (p-aminophenyl)methanesulfonyl fluoride (APMSF)). After insoluble materials were removed by centrifugation, the membrane proteins (20 µg) were incubated at 37° C. for 1 h with 3 units of each recombinant human caspase (Biovision) in 100 µl of 50 mM Hepes-NaOH (pH 7.4), 50 mM NaCl, 5% (v/v) glycerol, 5 mM DTT, 10 mM EDTA, 0.1 mM APMSF, and 0.1% CHAPS, and analyzed by Western blotting.

(13) Western Blotting

The cells were lysed in RIPA buffer (50 mM Hepes-NaOH buffer [pH 8.0] containing 1% NP-40, 0.1% SDS, 0.5% sodium deoxycholate, 150 mM NaCl, and 10% protease inhibitor cocktail). The lysates were mixed with 5×SDS sample buffer (200 mM Tris-HCl [pH 6.8], 10% SDS, 25% glycerol, 5% β-mercaptoethanol, and 0.05% bromophenol-blue), and incubated at room temperature for 1 h to detect Xkr8-GFP, or boiled for 5 min to detect other proteins. Proteins were separated by electrophoresis on a 10-20% gradient SDS-PAGE (Bio Craft), and transferred to a PVDF membrane (Millipore). The membranes were probed with 3000-fold-diluted mouse anti-GFP mAb, 3000-fold-diluted mouse anti-human ICAD mAb, or 3000-fold-diluted rabbit anti-active caspase 3 mAb followed by incubation with 1,000-fold-diluted HRP-conjugated goat anti-mouse or rabbit immunoglobulins (Dako). The peroxidase activity was detected by the Western Lightning™-ECL system (PerkinElmer).

2. Results (1) Cloning of Mouse Xkr8

Figure 1A:
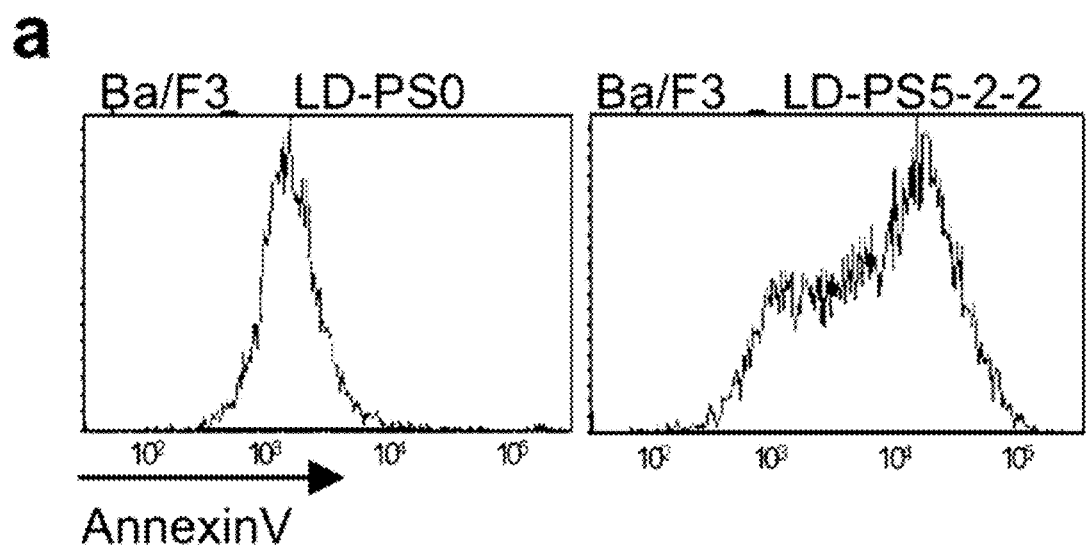
FIG. 1a: Molecular cloning and characterization of Xkr8 (a). Ba/F3 and its subline LD-PS5-2-2 cells were stained with Cy5-Annexin V.

By repeated FACS sorting and expansion of cells that efficiently exposed PtdSer, we previously established a subline of mouse Ba/F3 cells (Ba/F3-PS19) that exposes PtdSer at a high level[15]. TMEM16F, a $Ca^{2+}$-dependent phospholipid scramblase, was cloned from a Ba/F3-PS19 cDNA library constructed with cDNAs larger than 2.5 kb. To search for the scramblase responsible for apoptotic PtdSer exposure, a cDNA library was prepared with Ba/F3-PS19 cDNAs of 1.0 to 2.5 kb long, and introduced into Ba/F3 cells. FACS sorting and expansion of the cells that efficiently exposed PtdSer was repeated 5 times, and the sorted cells were subjected to limiting dilution. Using this process, we established a cell line (LD-PS5-2-2) that constitutively exposed PtdSer (FIG. 1a). The LD-PS5-2-2 cells carried a single integrated cDNA that codes for mouse Xkr8, a protein of 401 amino acids with several transmembrane segments.

Figure 1B:
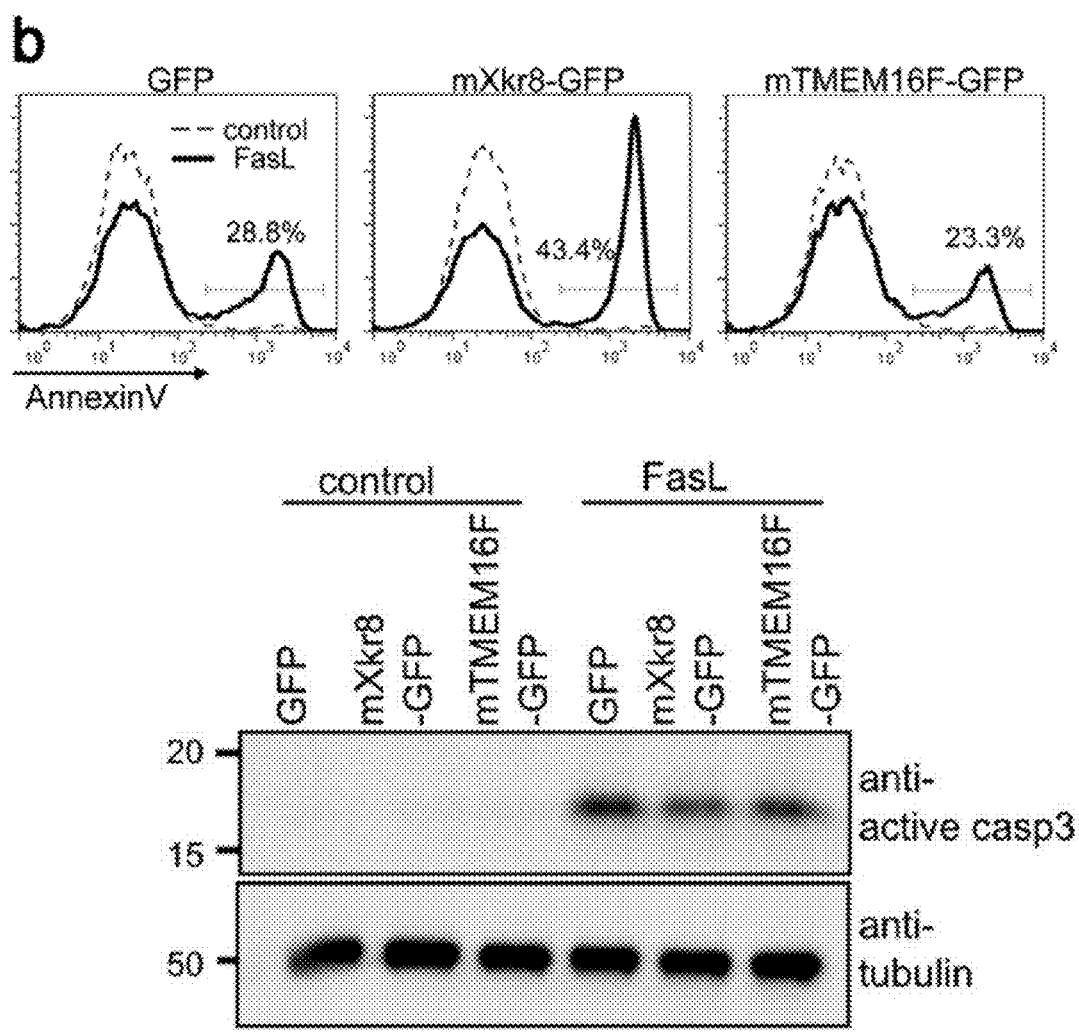
FIG. 1b: Molecular cloning and characterization of Xkr8 (b). WR-Fas and its mXkr8-GFP- or mTMEM16F-GFP-expressing transformants were treated with FasL and stained with Cy5-Annexin V. In bottom, the cell lysates were analyzed with anti-caspase 3 and anti-α-tubulin.
Figure 1D:
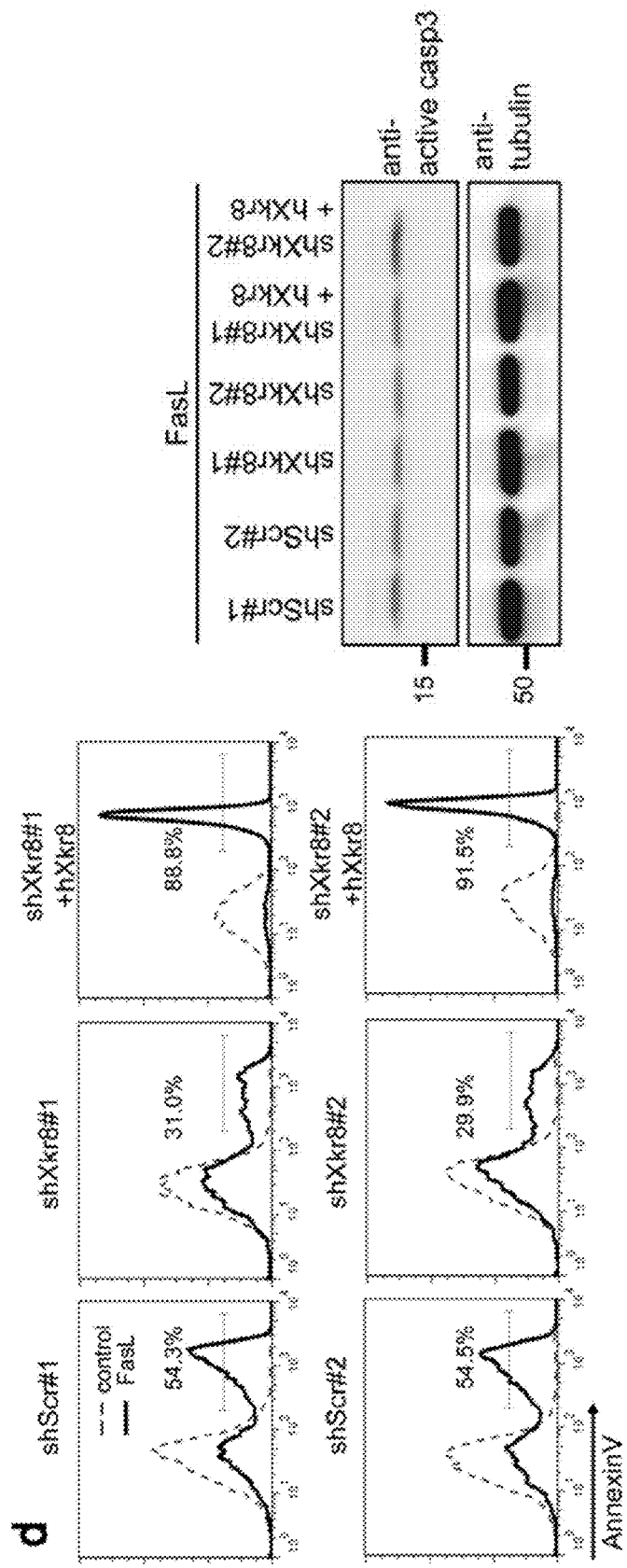
FIG. 1d: Molecular cloning and characterization of Xkr8 (d). WR-Fas, its mXkr8 shRNA-expressing transformants, and cells transformed further with hXkr8, two clones each, were treated with FasL and stained with Cy5-Annexin V. At right, the cell lysates were analyzed with anti-caspase 3 and anti-α-tubulin.
Figure 1E:
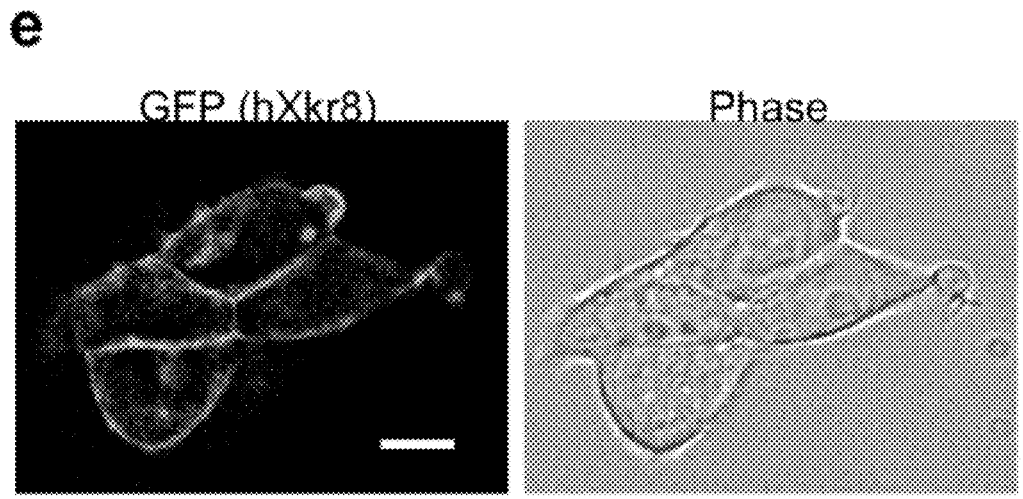
FIG. 1e: Molecular cloning and characterization of Xkr8 (e). 293T cell transformants with hXkr8-GFP were observed by fluorescence microscopy. Scale bar, 10 μm.

To examine whether Xkr8 is involved in apoptotic PtdSer exposure, Ba/F3 line and mouse T-cell line (WR19L) that expressed mouse Fas were established (BaF-Fas and WR-Fas). Fas ligand (FasL) efficiently induced the apoptosis of WR-Fas cells, accompanied by the caspase-3 activation and PtdSer exposure. This FasL-induced PtdSer exposure was strongly enhanced by transforming the cells with mouse (m) Xkr8-GFP but not with mTMEM16F-GFP (FIG. 1b). The endogenous mXkr8 gene expression in BaF-Fas and WR-Fas was then knocked down by expressing the mXkr8 short hairpin RNA (shRNA). The mXkr8 mRNA expression levels in transformants expressing the shRNA decreased to 18-24% of their levels in WR-Fas and BaF-Fas cells expressing a control shRNA (FIG. 1c and FIG. 7a). Accordingly, the FasL-induced PtdSer exposure was slowed in these transformants, although caspase 3 was activated similarly as in the parental cells (FIG. 1d). Human (h) Xkr8 cDNA, of which the sequence corresponding to the shRNA differs from mXkr8, fully rescued the inhibitory effect of mXkr8 shRNA (FIG. 1d, FIG. 7b). Observation of human 293T cell transformants expressing mXkr8-GFP (FIG. 1e) suggested that hXkr8 was located at the plasma membrane. These results indicated that Xkr8 at the plasma membrane could be a phospholipid scramblase activated by apoptotic stimuli.

(2) Epigenetic Control of Human Xkr8 Expression

Figure 2A:
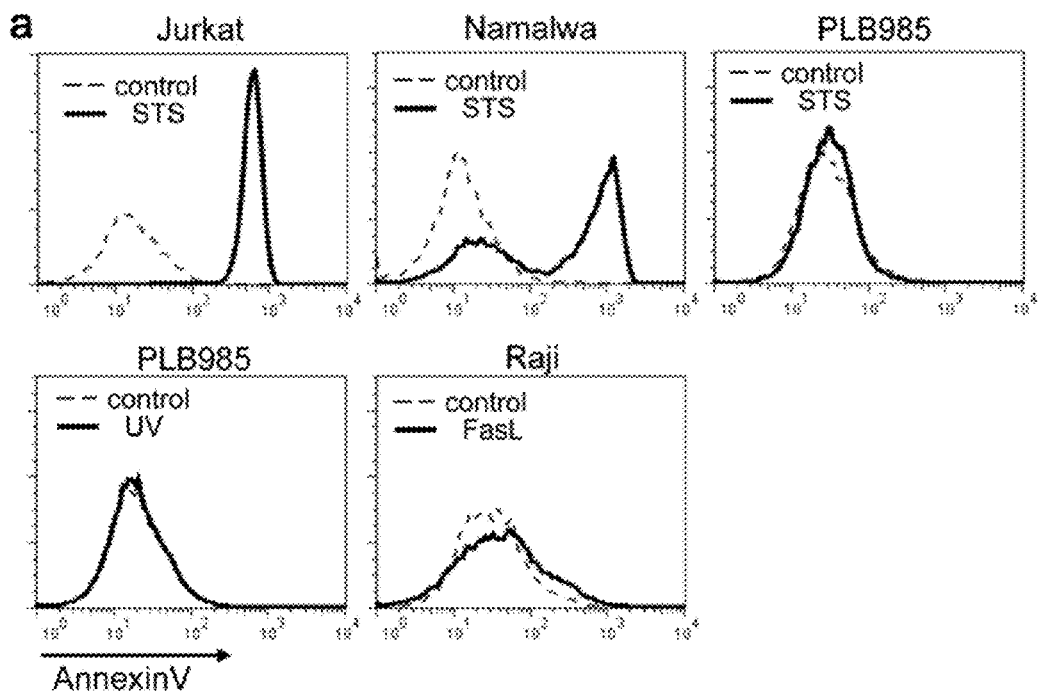
FIG. 2a: No Xkr8 expression in PLB-985 or Raji cells (a). Jurkat, Namalwa, PLB-985, and Raji cells were treated with staurosporine (STS), UV or FasL, and stained with Cy5-Annexin V.
Figure 2B:
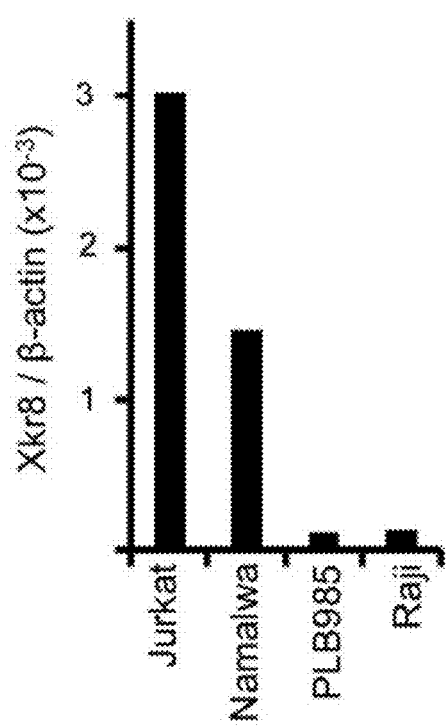
FIG. 2b: No Xkr8 expression in PLB-985 or Raji cells (b). Xkr8 mRNA levels in Jurkat, Namalwa, PLB-985, and Raji cells were determined by real-time RT-PCR.

In agreement with previous reports[17,18], human PLB-985 leukemia and Raji lymphoma lines did not expose PtdSer upon apoptotic stimuli such as staurosporine, UV, or FasL, which is in sharp contrast to human Namalwa and Jurkat cells that responded to staurosporine by exposing PtdSer (FIG. 2a). Real-time RT-PCR analysis indicated that the Xkr8 mRNA levels in the PLB-985 and Raji cells were 8 and 9% of that in Namalwa cells (FIG. 2b), respectively. When the PLB-985 or Raji cells were transfected with an hXkr8 expression plasmid, the transformants efficiently responded to staurosporine, UV-irradiation or FasL by exposing PtdSer, without enhancement of caspase activation (FIG. 2c). These results indicated that the inability of PLB-985 and Raji cells to expose PtdSer was due to the lack of the Xkr8 gene expression.

Figure 3A:
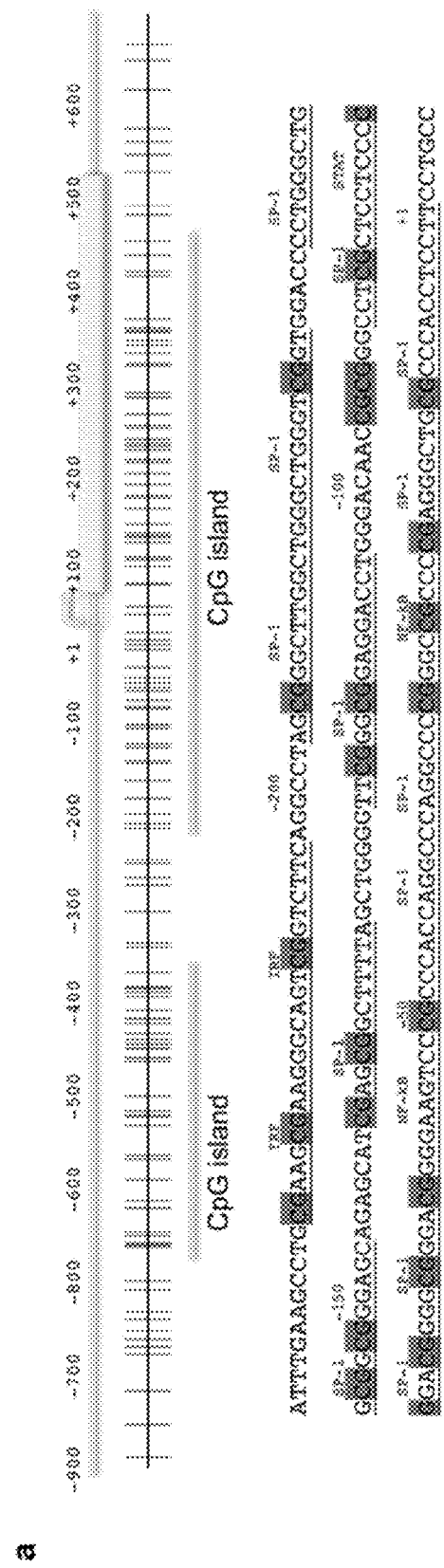
FIG. 3a: Epigenetic control of Xkr8 gene expression (a). CpG islands in the hXkr8 gene promoter. (Upper) exon 1 is indicated as a box. Open and filled areas represent the 5' non-coding and coding region, respectively. Arrow indicates the transcription start site. Each CpG site is indicated by a vertical bar, and CpG islands by horizontal lines. (Bottom) nucleotide sequence from −239 to +7 of the hXkr8 gene. The 23 CpGs are shaded, and transcription-recognition sites are underlined.

A PCR analysis showed no gross abnormality in the hXkr8 genomic structure in the PLB-985 cells. However, an analysis of the hXkr8 gene for the presence of CpG islands using the program "CpG island searcher" from the University of Southern California indicated two CpG islands in the 1.2-kb region near the transcription start site of the hXkr8 gene (FIG. 3a). The second island was in the promoter region, where recognition sites for the Sp1 and NF-κB transcription factors were clustered.

Figure 3B:
FIG. 3b: Epigenetic control of Xkr8 gene expression (b). Each circle represents a CpG site, and the extent of methylation was: black, 75-100%; grey, 26-75%; white, 0-25%.
Figure 3B:
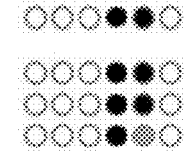
Figure 3B:
Figure 3B:
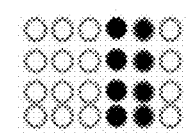
Figure 3B:
Figure 3B:
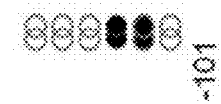
Figure 3B:
Figure 3B:
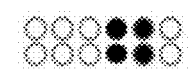
Figure 3B:
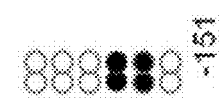
Figure 3B:
Figure 3B:
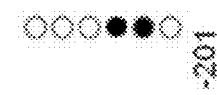
Figure 3B:
Figure 3B:
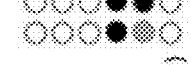
Figure 3B:
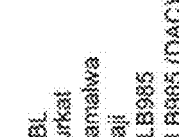
Figure 3B:
Figure 3D:
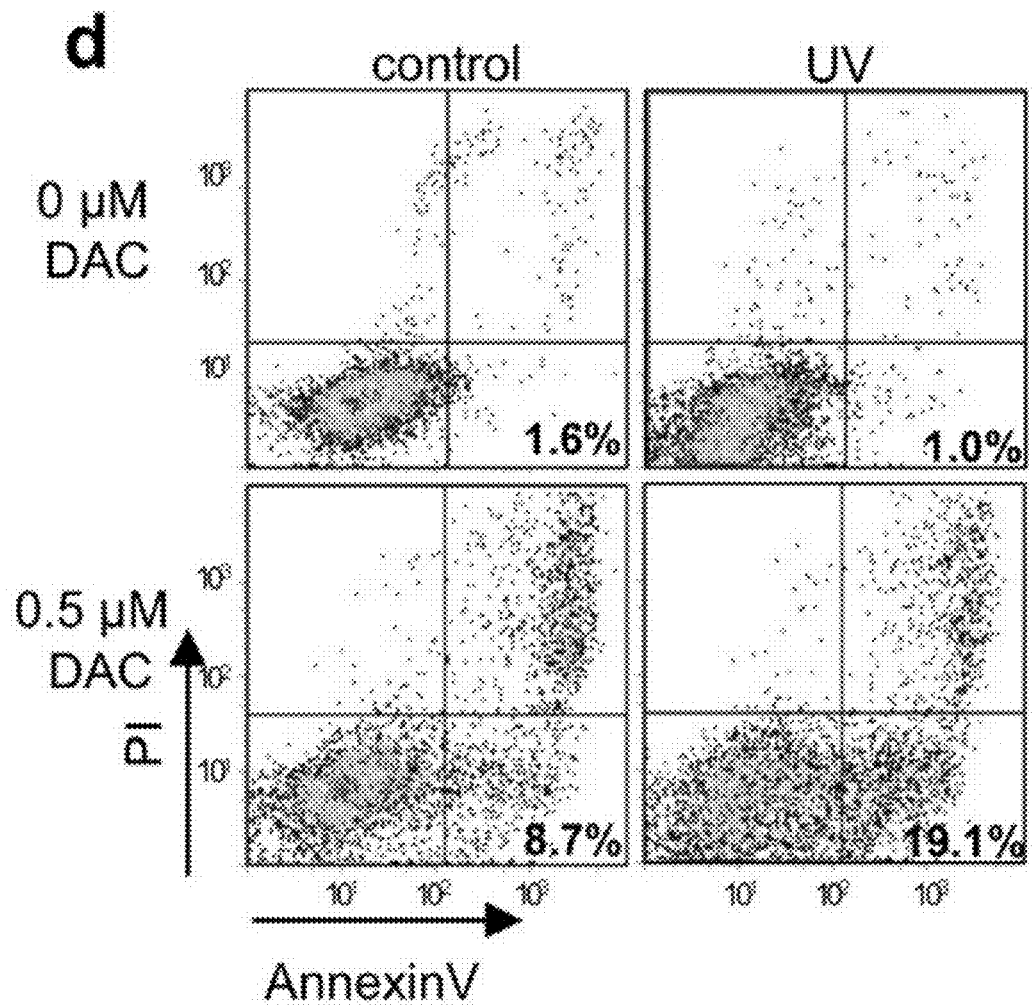
FIG. 3d: Epigenetic control of Xkr8 gene expression (d). Five days DAC-treated PLB-985 cells were exposed to UV, and stained with Cy5-Annexin V and PI.

To determine the methylation status of each CpG site between −239 and +7 of the hXkr8 gene, DNA was prepared from PLB-985, Raji, and Namalwa cells, and from peripheral blood leukocytes from a healthy person, and analyzed by bisulfite DNA sequencing[19]. None of the 23 CpG sites was methylated in the DNA from the peripheral blood leukocytes, Jurkat or Namalwa cells (FIG. 3b). In contrast, all the CpG sites were heavily, or with more than 90% probability, methylated in the PLB-985 and Raji cells. Treatment of the PLB-985 cells with a demethylating agent, 5-aza-2'-deoxycytidine (DAC), gradually increased their Xkr8 mRNA level (FIG. 3c). On day 7, all 23 of the CpG sites between −239 and +7 in the PLB-985 cells were highly demethylated (FIG. 3b), and the Xkr8 mRNA level reached about 91% of that in Namalwa cells (FIG. 3c). Accordingly, the DAC-treated PLB-985 cells gained the ability to expose PtdSer in response to UV irradiation (FIG. 3d). These results indicate that the CpG islands in the promoter region of the hXkr8 gene were heavily methylated in the PLB-985 and Raji cells, which blocked the Xkr8 gene expression, leading to the defective PtdSer exposure during apoptosis.

(3) The Xkr8-Mediated Scramblase Activity

Figure 4A:
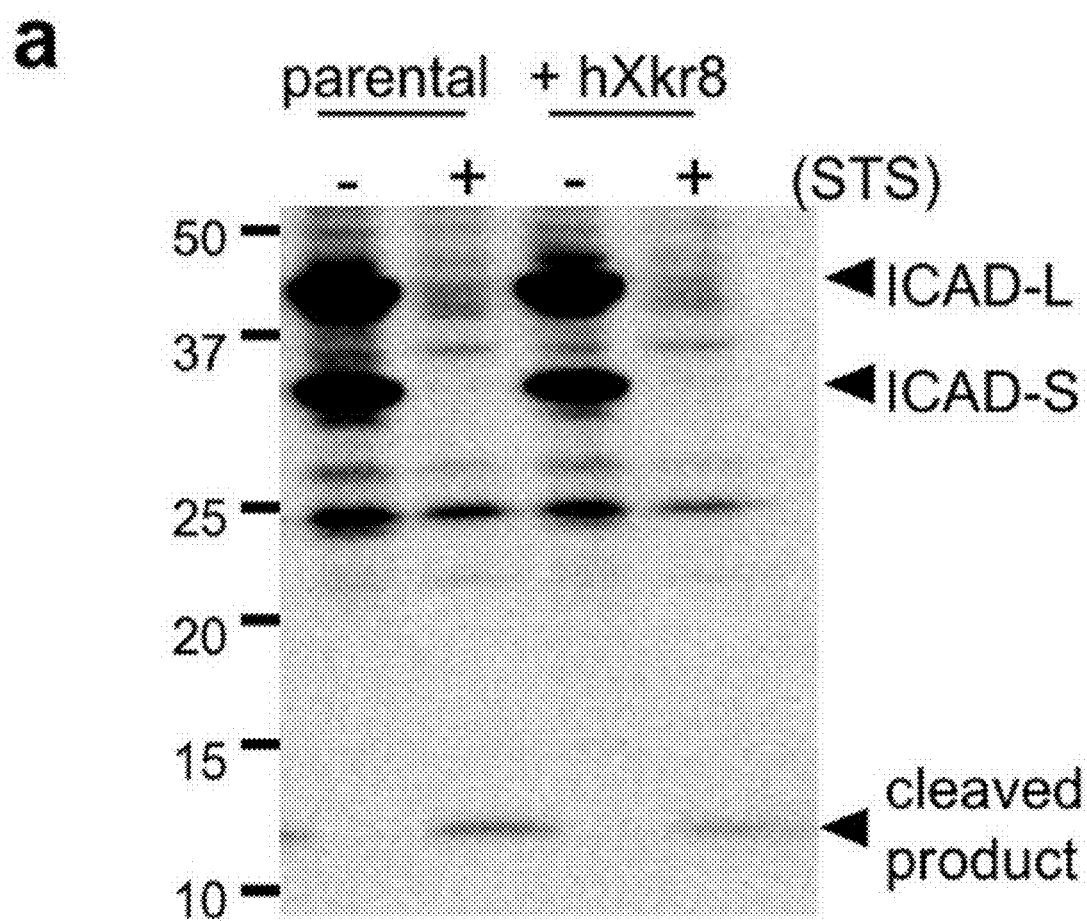
FIG. 4a: Characterization of the hXkr8-mediated scrambling activity (a). PLB-985 cells and its hXkr8-expressing transformants were treated with STS, and cell lysates were analyzed by Western blotting with anti-ICAD.
Figure 4B:
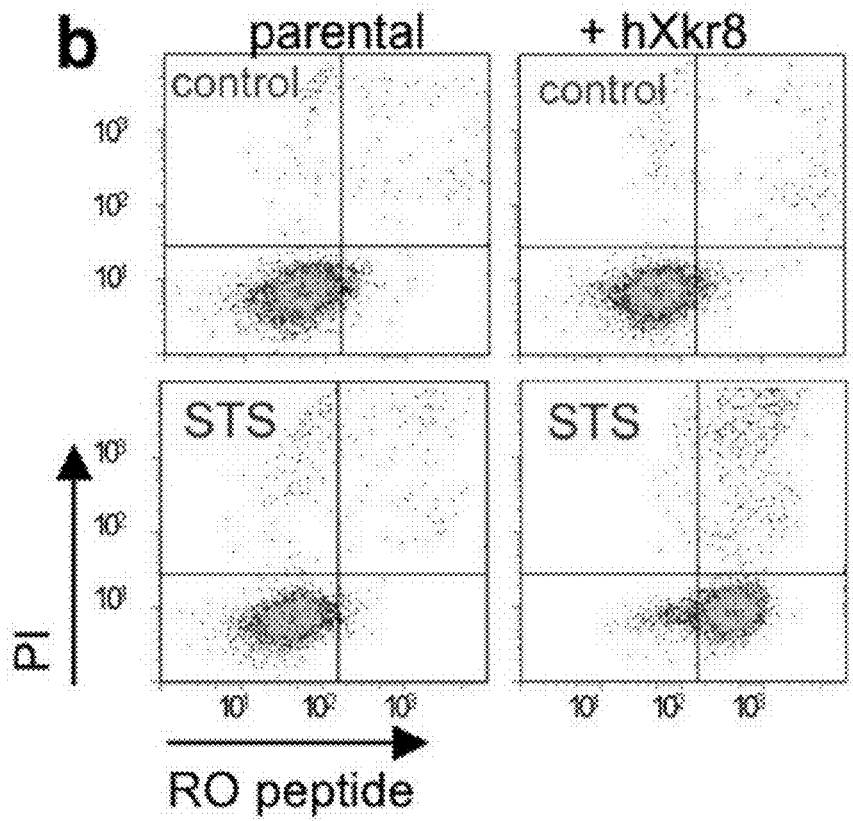
FIG. 4b: Characterization of the hXkr8-mediated scrambling activity (b). PLB-985 and its hXkr8-expressing transformants were treated with STS, stained with biotin-RO peptide and streptavidin-APC and PI, and analyzed by FACS.
Figure 4C:
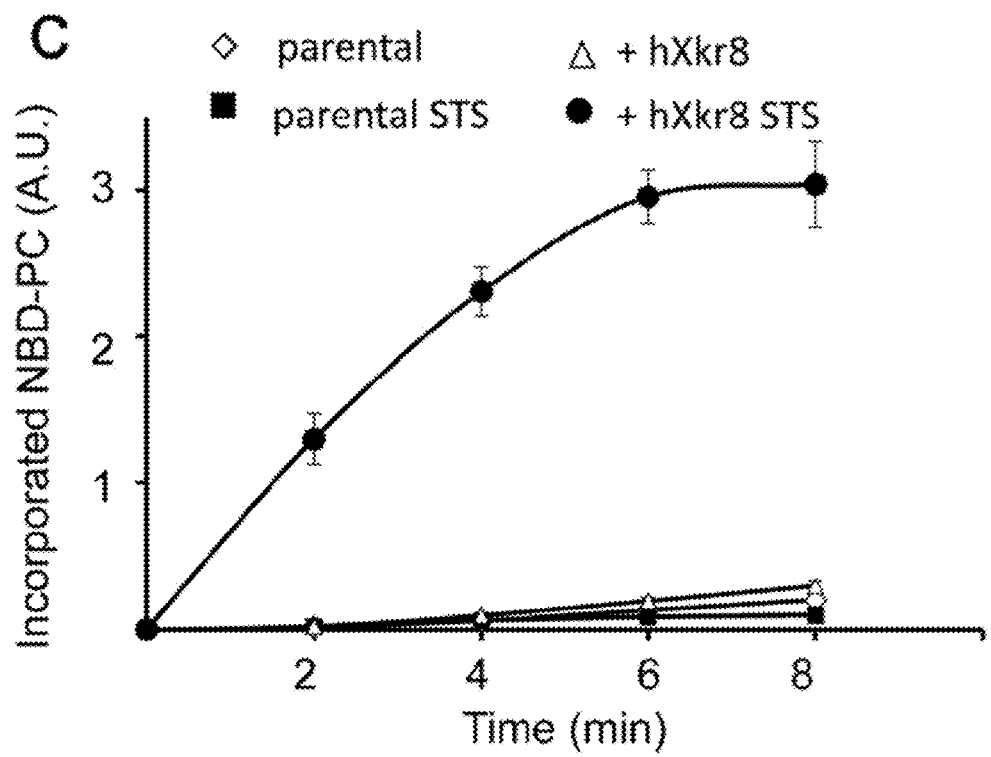
FIG. 4c: Characterization of the hXkr8-mediated scrambling activity (c). PLB-985 and its hXkr8-expressing transformants treated with STS, then incubated with NBD-PC. At various times, the unincorporated lipids were extracted, and analyzed by FACSAria. The fluorescence intensity in the SytoxBlue-negative fraction is shown in arbitrary units as the internalized NBD-PC.
Figure 4D:
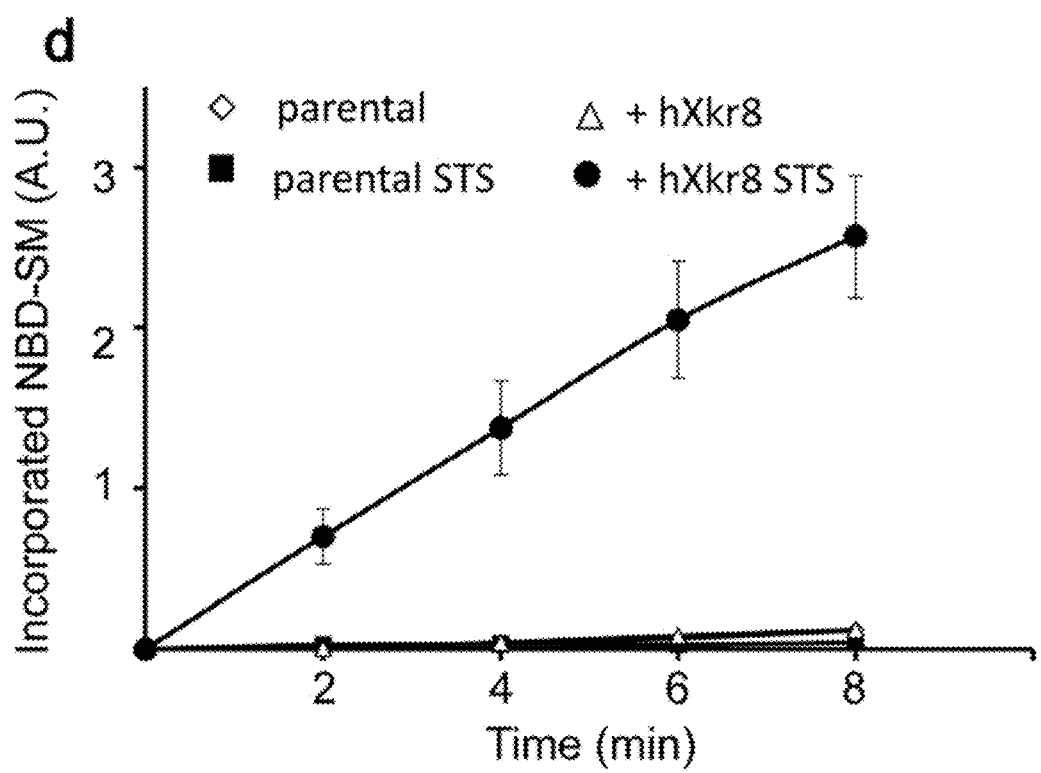
FIG. 4d: Characterization of the hXkr8-mediated scrambling activity (d). Cells were incubated with NBD-SM in the same way as described in FIG. 4c.

Phospholipid scramblase is defined as an enzyme that can non-specifically scramble phospholipids in the plasma membrane[20]. To characterize the scramblase activity mediated by Xkr8, human PLB-985 and its transformants expressing hXkr8 were treated with staurosporine. Four hours later, ICAD (ICAD-L and ICAD-S) was cleaved equally well in PLB-985 and its hXkr8-expressing transformant (FIG. 4a). As found for the PtdSer exposure, the parental PLB-985 cells and hXkr8 transformants did not expose PtdEtn when they were growing as recognized by the PtdEtn-binding peptide RO09-0198[21] (RO peptide) (FIG. 4b). Staurosporine-treated hXkr8-expressing PLB-985 cells, but not the parental cells, were stained with the RO peptide, indicating that PtdEtn was exposed. The scrambling activity for PtdCho and SM was examined by assaying the internalization of 1-oleoyl-2-{6-[(7-nitro-2-1,3-benzoxadiazol-4-yl)amino]hexanoyl}-sn-glycero-3-phosphocholine (NBD-PC), or N-[6-[(7-nitro-2-1,3-benzoxadiazol-4-yl)amino]hexanoyl]-sphingosine-1-phosphocholine (NBD-SM). As shown in FIGS. 4c and 4d, NBD-PC and NBD-SM were not internalized in the growing PLB-985 cells or the hXkr8 transformants. However, NBD-PC and NBD-SM were internalized in the staurosporine-treated hXkr8 transformants, but not in the parental cells. These results indicated that Xkr8 was activated during apoptotic cell death and served as a non-specific scramblase. This non-specific scrambling activity of Xkr8 is similar to that of TMEM16F, a $Ca^{2+}$-dependent phospholipid scramblase[15]. However, unlike the apoptosis-induced PtdSer exposure, the $Ca^{2+}$-induced PtdSer exposure occurred in the PLB-985 cells and the hXkr8 transformants with the same kinetics (FIG. 8), suggesting that Xkr8 had no effect on the $Ca^{2+}$-dependent PtdSer exposure.

Activation of Xkr8 by Caspase

Xkr8 is a member of the XK family[22], and its homologues are present in mammals, fishes, and amphibians (FIG. 5a). Analyses of the amino acid sequences of Xkr8 from various species with topology prediction programs including TMpred and TMHMM yielded inconsistent predictions of six to eight transmembrane regions. Assuming that the overall structure of the Xkr8 protein is conserved among species, it is tentatively ascertained that Xkr8 carries six transmembrane regions with cytosolic N- and C-termini (FIG. 5b). Using the online search tool (CASVM), a well-conserved caspase 3-recognition sequence[23] was identified in the C-terminal cytoplasmic region of human, mouse, rat, fugu, medaka, and Xenopus Xkr8 (FIG. 5a).

Apoptotic PtdSer exposure is caspase-dependent in many cases[24]. The presence of a caspase recognition sequence in Xkr8 suggested that Xkr8 could be a direct target of caspase 3. To examine whether the cleavage of Xkr8 at this position was required for its scrambling activity, the PDQVDG sequence at amino-acid position 355 of hXkr8 was mutated to PAQVAG (2DA) (FIG. 5c), fused to GFP at its C-terminus, and introduced into PLB-985 cells. In contrast to PLB-985 transformant expressing wild-type hXkr8-GFP, the cells transformed by the 2DA mutant hXkr8-GFP showed almost no PtdSer exposure in response to staurosporine (FIG. 5d). To confirm that hXkr8 was cleaved during apoptosis, PLB-985 cells expressing hXkr8-GFP were treated with staurosporine, then analyzed by Western blotting with anti-GFP antibody (FIG. 5e). In growing cells, hXkr8-GFP showed a band of 52 kDa, the size of the hXkr8-GFP fusion protein. When the cells were treated with staurosporine, the 52 kDa band shifted to 29 kDa, which was slightly larger than authentic GFP. On the other hand, the 2DA mutant of hXkr8 was barely processed by staurosporine treatment. Endogenous ICAD was cleaved similarly in PLB-985 transformants expressing the wild-type or caspase-resistant hXkr8, indicating that caspase 3 was activated equally in them. Similar processing of mXkr8 at the caspase-recognition site (PDLVDG at position 354) during apoptotic cell death was observed when WR-Fas cells expressing the wild-type mXkr8-GFP fusion protein were treated with FasL (FIG. 5f). The Triton X-100-solubilized membrane fraction was then prepared from cells expressing the GFP-fusion protein, and incubated with various recombinant human caspases. Western blot analysis with anti-GFP antibody showed that caspase 3 and caspase 7 cleaved the wild-type but not 2DA mutant hXkr8 (FIG. 5g). These results indicated that cleavage of hXkr8 at Asp-355 or of mXkr8 at Asp-354 in the C-terminal tail enabled the molecule to function as a phospholipid scramblase.

Next, hXkr8 was truncated at Asp-355 (FIG. 5c) and introduced into PLB-985 cells with or without fused GFP to examine whether it acted as a constitutively active form. However, the truncated hXkr8s did not mediate PtdSer exposure in either growing or apoptotic cells (FIG. 5d). Fluorescence microscopy of human 293T cells expressing the truncated hXkr8-GFP fusion protein showed that it to be present in the cytoplasm, probably in the endoplasmic reticulum (FIG. 5h). A motif of dibasic [R/K(X)R/K] or diaromatic amino acids (FF, FY or YY) present in various transmembrane proteins serves as an endoplasmic reticulum export signal[25,26]. There were two or three of these motifs in the Xkr8 cytoplasmic tail of all the species listed in FIG. 5a. Since these motifs were located downstream of the caspase-recognition site in hXkr8, it is likely that the truncated hXkr8 could not be transported to the plasma membrane.

Xkr8$^{-/-}$ Foetal Thymocyte Cell Line

PtdSer is exposed on the cell surface of most cells undergoing apoptosis. Accordingly, mXkr8 mRNA was ubiquitously and similarly expressed in various mouse tissues (FIG. 6a), except that it was extremely high in the testis, and low in the heart and muscle. To confirm Xkr8's role in phospholipid scrambling, and to compare its phospholipid scrambling activity with that of TMEM16F, an Xkr8-deficient foetal thymocyte cell line (IFET) was established (FIG. 6b). In response to FasL, the Xkr8$^{flox/flox}$ and TMEM16F$^{-/-}$ IFET cells quickly exposed PtdSer (FIG. 6c). In contrast, Xkr8$^{-/-}$ IFET cells did not expose PtdSer in response to this treatment, although caspase 3 was similarly activated. When the Xkr8$^{-/-}$ IFET cells were infected by a retrovirus carrying mXkr8 cDNA, the transformants exposed PtdSer in response to FasL. In contrast, Ca$^{2+}$ ionophore induced PtdSer exposure in the Xkr8$^{flox/flox}$ and Xkr8$^{-/-}$, but not in the TMEM16F$^{-/-}$ IFET cells (FIG. 6d). These results indicate that Xkr8 is responsible for the apoptotic PtdSer exposure, while TMEM16F is responsible for Ca$^{2+}$-induced PtdSer exposure.

REFERENCES

1. Jacobson, M. D., Well, M., & Raff, M. C., Programmed cell death in animal development. Cell 88, 347-354 (1997).
2. Vaux, D. L. & Korsmeyer, S. J., Cell death in development. Cell 96, 245-254 (1999).
3. Nagata, S., Apoptosis by death factor. Cell 88, 355-365 (1997).
4. Strasser, A., O'Connor, L., & Dixit, V. M., Apoptosis signaling. Annu. Rev. Biochem. 69, 217-245 (2000).
5. Nagata, S., DNA degradation in development and programmed cell death. Annu. Rev. Immunol. 23, 853-875 (2005).
6. Enari, M. et al., A caspase-activated DNase that degrades DNA during apoptosis, and its inhibitor ICAD. Nature 391, 43-50 (1998).
7. Coleman, M. et al., Membrane blebbing during apoptosis results from caspase-mediated activation of ROCK I. Nat. Cell Biol. 3, 339-345 (2001).
8. Sebbagh, M. et al., Caspase-3-mediated cleavage of ROCK I induces MLC phosphorylation and apoptotic membrane blebbing. Nat. Cell Biol. 3, 346-352 (2001).
9. Fadok, V. A. et al., Exposure of phosphatidylserine on the surface of apoptotic lymphocytes triggers specific recognition and removal by macrophages. J. Immunol. 148, 2207-2216 (1992).
10. Leventis, P. A. & Grinstein, S., The Distribution and Function of Phosphatidylserine in Cellular Membranes. Annu. Rev. Biophys. 39, 407-427 (2010).
11. Ravichandran, K. S. & Lorenz, U., Engulfment of apoptotic cells: signals for a good meal. Nat. Rev. Immunol. 7, 964-974 (2007).
12. Nagata, S., Hanayama, R., & Kawane, K., Autoimmunity and the clearance of dead cells. Cell 140, 619-630 (2010).
13. Zwaal, R., Comfurius, P., & Bevers, E., Lipid-protein interactions in blood coagulation. Biochim. Biophys. Acta 1376, 433-453 (1998).
14. Bevers, E. & Williamson, P., Phospholipid scramblase: an update. FEBS Lett. 584, 2724-2730 (2010).
15. Suzuki, J., Umeda, M., Sims, P. J., & Nagata, S., Calcium-dependent phospholipid scrambling by TMEM16F. Nature 468, 834-838 (2010).
16. Williamson, P. et al., Phospholipid scramblase activation pathways in lymphocytes. Biochemistry 40, 8065-8072 (2001).
17. Fadeel, B. et al., Phosphatidylserine exposure during apoptosis is a cell-type-specific event and does not correlate with plasma membrane phospholipid scramblase expression. Biochem. Biophys. Res. Commun. 266, 504-511 (1999).
18. Fadok, V. A., de Cathelineau, A., Daleke, D. L., Henson, P. M., & Bratton, D. L., Loss of phospholipid asymmetry and surface exposure of phosphatidylserine is required for phagocytosis of apoptotic cells by macrophages and fibroblasts. J. Biol. Chem. 276, 1071-1077 (2001).
19. Herman, J. G., Graff, J. R., Myohanen, S., Nelkin, B. D., & Baylin, S. B., Methylation-specific PCR: a novel PCR assay for methylation status of CpG islands. Proc. Natl. Acad. Sci. USA 93, 9821-9826 (1996).
20. Balasubramanian, K. & Schroit, A., Aminophospholipid asymmetry: A matter of life and death. Annu. Rev. Physiol. 65, 701-734 (2003).
21. Emoto, K., Toyama-Sorimachi, N., Karasuyama, H., Inoue, K., & Umeda, M., Exposure of phosphatidylethanolamine on the surface of apoptotic cells. Exp. Cell Res. 232, 430-434 (1997).
22. Calenda, G. et al., Identification of two new members, XPLAC and XTES, of the XK family. Gene 370, 6-16 (2006).
23. Timmer, J. C. & Salvesen, G. S., Caspase substrates. Cell Death Differ. 14, 66-72 (2007).

24. Martin, S. J., Finucane, D. M., Amarante-Mendes, G. P., O'Brien, G. A., & Green, D. R., Phosphatidylserine externalization during CD95-induced apoptosis of cells and cytoplasts requires ICE/CED-3 protease activity. J. Biol. Chem. 271, 28753-28756 (1996).
25. Giraudo, C. G. & Maccioni, H. J. F., Endoplasmic reticulum export of glycosyltransferases depends on interaction of a cytoplasmic dibasic motif with Sarl. Mol. Biol. Cell. 14, 3753-3766 (2003).
26. Barlowe, C., Signals for COPII-dependent export from the ER: what's the ticket out? Trends Cell Biol. 13, 295-300 (2003).
27. Ho, M. et al., Isolation of the gene for McLeod syndrome that encodes a novel membrane transport protein. Cell 77, 869-880 (1994).
28. Russo, D., Redman, C., & Lee, S., Association of XK and Kell blood group proteins. The Journal of biological chemistry 273, 13950-13956 (1998).
29. Schoenwaelder, S. M. et al., Two distinct pathways regulate platelet phosphatidylserine exposure and procoagulant function. Blood 114, 663-666 (2009).
30. Ricci, J.-E. et al., Disruption of mitochondrial function during apoptosis is mediated by caspase cleavage of the p75 subunit of complex I of the electron transport chain. Cell 117, 773-786 (2004).
31. Gleiss, B., Gogvadze, V., Orrenius, S., & Fadeel, B., Fas-triggered phosphatidylserine exposure is modulated by intracellular ATP. FEBS Lett. 519, 153-158 (2002).
32. Fadeel, B. & Orrenius, S., Apoptosis: a basic biological phenomenon with wide-ranging implications in human disease. J. Inter. Med. 258, 479-517 (2005).
33. Sandilos, J. K. et al., Pannexin 1, an ATP Release Channel, Is Activated by Caspase Cleavage of Its Pore-associated C-terminal Autoinhibitory Region. J. Biol. Chem. 287, 11303-11311 (2012).
34. Chekeni, F. B. et al., Pannexin 1 channels mediate 'find-me' signal release and membrane permeability during apoptosis. Nature 467, 863-867 (2010).
35. Bratton, D. et al., Appearance of phosphatidylserine on apoptotic cells requires calcium-mediated nonspecific flip-flop and is enhanced by loss of the aminophospholipid translocase. J. Biol. Chem. 272, 26159-26165 (1997).
36. Hampton, M., Vanags, D., Porn-Ares, M., & Orrenius, S., Involvement of extracellular calcium in phosphatidylserine exposure during apoptosis. FEBS Lett. 399, 277-282 (1996).
37. van den Eijnde, S. et al., Cell surface exposure of phosphatidylserine during apoptosis is phylogenetically conserved. Apoptosis 3, 9-16 (1998).
38. Venegas, V. & Zhou, Z., Two alternative mechanisms that regulate the presentation of apoptotic cell engulfment signal in *Caenorhabditis elegans*. Mol. Biol. Cell 18, 3180-3192 (2007).
39. Ellis, R. E., Jacobson, D. M., & Horvitz, H. R., Genes required for the engulfment of cell corpses during programmed cell death in *Caenorhabditis elegans*. Genetics 129, 79-94. (1991).
40. Stanfield, G. & Horvitz, H., The ced-8 gene controls the timing of programmed cell deaths in *C. elegans*. Mol. Cell 5, 423-433 (2000).
41. Munoz, L. E., Lauber, K., Schiller, M., Manfredi, A. A., & Herrmann, M., The role of defective clearance of apoptotic cells in systemic autoimmunity. Nat. Rev. Rheumatol. 6, 280-289 (2010).
42. Franks, A. L. & Slansky, J. E., Multiple associations between a broad spectrum of autoimmune diseases, chronic inflammatory diseases and cancer. Anticancer Res. 32, 1119-1136 (2012).
43. Yoshida, H. et al., Phosphatidylserine-dependent engulfment by macrophages of nuclei from erythroid precursor cells. Nature 437, 754-758 (2005).
44. Connor, J., Pak, C. C., & Schroit, A. J., Exposure of phosphatidylserine in the outer leaflet of human red blood cells. Relationship to cell density, cell age, and clearance by mononuclear cells. J. Biol. Chem. 269, 2399-2404 (1994).
45. Stowell, S. R. et al., Galectin-1 induces reversible phosphatidylserine exposure at the plasma membrane. Mol. Biol. Cell 20, 1408-1418 (2009).
46. van den Eijnde, S. et al., Transient expression of phosphatidylserine at cell-cell contact areas is required for myotube formation. J. Cell Sci. 114, 3631-3642 (2001).
47. Gadella, B. & Harrison, R., Capacitation induces cyclic adenosine 3',5'-monophosphate-dependent, but apoptosis-unrelated, exposure of aminophospholipids at the apical head plasma membrane of boar sperm cells. Biol. Reprod. 67, 340-350 (2002).
48. Marguet, D., Luciani, M. F., Moynault, A., Williamson, P., & Chimini, G., Engulfment of apoptotic cells involves the redistribution of membrane phosphatidylserine on phagocyte and prey. Nat. Cell Biol. 1, 454-456 (1999).
49. Imao, T. & Nagata, S., Apaf-1- and Caspase-8-independent apoptosis. Cell Death Differ, in press (2012).
50. Palacios, R. & Steinmetz, M., Il-3-dependent mouse clones that express B-220 surface antigen, contain Ig genes in germ-line configuration, and generate B lymphocytes in vivo. Cell 41, 727-734 (1985).
51. Tucker, K. A., Lilly, M. B., Heck, L., & Rado, T. A., Characterization of a new human diploid myeloid leukemia cell line (PLB-985) with granulocytic and monocytic differentiating capacity. Blood 70, 372-378 (1987).
52. Morita, S., Kojima, T., & Kitamura, T., Plat-E: an efficient and stable system for transient packaging of retroviruses. Gene Ther. 7, 1063-1066 (2000).
53. Fukunaga, R., Ishizaka-Ikeda, E., & Nagata, S., Purification and characterization of the receptor for murine granulocyte colony-stimulating factor. J. Biol. Chem. 265, 14008-14015 (1990).
54. Shiraishi, T. et al., Increased cytotoxicity of soluble Fas ligand by fusing isoleucine zipper motif. Biochem. Biophys. Res. Commun. 322, 197-202 (2004).
55. Suzuki, J., Umeda, M., Sims, P. J., & Nagata, S., Calcium-dependent phospholipid scrambling by TMEM16F. Nature 468, 834-838 (2010).
56. Kitamura, T. et al., Retrovirus-mediated gene transfer and expression cloning: powerful tools in functional genomics. Exp. Hematol. 31, 1007-1014 (2003).
57. Higuchi, R., Recombinant PCR in PCR protocols: A guide to methods and applications (Academic Press, San Diego, 1990), pp. 177-188.
58. Kontgen, F., Suss, G., Stewart, C., Steinmetz, M., & Bluethmann, H., Targeted disruption of the MHC class II Aa gene in C57BL/6 mice. Int. Immunol. 5, 957-964 (1993).
59. Kanki, H., Suzuki, H., & Itohara, S., High-efficiency CAG-FLPe deleter mice in C57BL/6J background. Exp. Anim. 55, 137-141 (2006).
60. Cattermole, J. A. et al., Isolation of murine fetal thymus cell lines after infection with recombinant retroviruses containing the v-myc and v-Ha-ras oncogenes. J. Immunol. 142, 3746-3753 (1989).

61. Imao, T. & Nagata, S., Apaf-1- and Caspase-8-independent apoptosis. Cell Death Differ, in press (2012).
62. Akagi, T., Sasai, K., & Hanafusa, H., Refractory nature of normal human diploid fibroblasts with respect to oncogene-mediated transformation. Proc. Natl. Acad. Sci. USA 100, 13567-13572 (2003).
63. Watson, J. D., Morrissey, P. J., Namen, A. E., Conlon, P. J., & Widmer, M. B., Effect of IL-7 on the growth of fetal thymocytes in culture. J. Immunol. 143, 1215-1222 (1989).
64. Watanabe-Fukunaga, R. et al., The cDNA structure, expression, and chromosomal assignment of the mouse Fas antigen. J. Immunol. 148, 1274-1279 (1992).
65. Ogasawara, J. et al., Lethal effect of the anti-Fas antibody in mice. Nature 364, 806-809 (1993).
66. Aoki, Y., Uenaka, T., Aoki, J., Umeda, M., & Inoue, K., A novel peptide probe for studying the transbilayer movement of phosphatidylethanolamine. J. Biochem. 116, 291-297 (1994).
67. Herman, J. G., Graff, J. R., Myohanen, S., Nelkin, B. D., & Baylin, S. B., Methylation-specific PCR: a novel PCR assay for methylation status of CpG islands. Proc. Natl. Acad. Sci. USA 93, 9821-9826 (1996).

SEQUENCE FREE TEXT

SEQ ID NO: 7: Synthetic primer
SEQ ID NO: 8: Synthetic primer
SEQ ID NO: 9: Synthetic primer
SEQ ID NO: 10: Synthetic primer
SEQ ID NO: 11: Synthetic primer
SEQ ID NO: 12: Synthetic primer
SEQ ID NO: 13: Synthetic primer
SEQ ID NO: 14: Synthetic primer
SEQ ID NO: 15: Synthetic primer
SEQ ID NO: 16: Target sequence of shRNA
SEQ ID NO: 17: Synthetic primer
SEQ ID NO: 18: Synthetic primer
SEQ ID NO: 19: Synthetic primer
SEQ ID NO: 20: Synthetic primer
SEQ ID NO: 21: Synthetic primer
SEQ ID NO: 22: Synthetic primer
SEQ ID NO: 23: Synthetic primer
SEQ ID NO: 24: Synthetic primer
SEQ ID NO: 25: Synthetic primer
SEQ ID NO: 26 Synthetic primer
SEQ ID NO: 27: Synthetic primer
SEQ ID NO: 28: Synthetic primer
SEQ ID NO: 29: Synthetic primer

The invention claimed is:

1. A method of screening an agent potentiating or inhibiting a biological function of XK-related protein 8 (Xkr8) as a lipid scramblase comprising the steps of:
   (1) treating Xkr8-expressing mammalian cells having a plasma membrane comprising an inner leaflet and an outer leaflet into which a gene encoding and expressing XKr8 has been introduced, with a candidate of the agent in the presence of an apoptotic stimulus, and
   (2) determining whether the candidate alters a distribution of a lipid selected from the group consisting of phosphatidylserine, phosphatidylethanolamine, phosphatidylcholine, and sphingomyelin in the inner leaflet or the outer leaflet of the plasma membrane of the treated cells,
   wherein a candidate which significantly increases the distribution of phosphatidylserine or phosphatidylethanolamine in the outer leaflet of the plasma membrane compared to a control is selected as an agent potentiating the biological function of Xkr8 as a lipid scramblase; wherein a candidate which significantly decreases the distribution of phosphatidylserine or phosphatidylethanolamine in the outer leaflet of the plasma membrane compared to a control is selected as an agent inhibiting the biological function of Xkr8 as a lipid scramblase; wherein a candidate which significantly increases the distribution of phosphatidylcholine or sphingomyelin in the inner leaflet of the plasma membrane compared to a control is selected as an agent potentiating the biological function of Xkr8 as a lipid scramblase; and wherein a candidate which significantly decreases the distribution of phosphatidylcholine or sphingomyelin in the inner leaflet of the plasma membrane compared to a control is selected as an agent inhibiting the biological function of Xkr8 as a lipid scramblase;
   wherein the distribution of phosphatidylserine in the plasma membrane is determined by detecting the binding between phosphatidylserine exposed on the cell surface and an agent having phosphatidylserine-binding property or the distribution of phosphatidylserine in the plasma membrane is determined by measuring the production of thrombin or fibrin; the distribution of phosphatidylethanolamine in the plasma membrane is determined by detecting the binding between phosphatidylethanolamine exposed on the cell surface and an agent having phosphatidylethanolamine-binding property; and the distribution of phosphatidylcholine or sphingomyelin in the plasma membrane if determined by a fluorescently labeled lipid.

2. The method of claim 1, wherein the method is for screening an agent for the treatment of an apoptosis-related disease.

3. The method of claim 2, wherein the apoptosis-related disease is an autoimmune disease.

4. The method of claim 2, wherein the apoptosis-related disease is cancer.

5. The method of claim 1, wherein the Xkr8-expressing mammalian cells are human, monkey, mouse, or rabbit cells.

* * * * *

SEQUENCE LISTING

```
<160> NUMBER OF SEQ ID NOS: 29

<210> SEQ ID NO 1
<211> LENGTH: 401
<212> TYPE: PRT
<213> ORGANISM: Mus musculus

<400> SEQUENCE: 1

Met Pro Leu Ser Val His His Val Ala Leu Asp Val Val Gly
1               5                   10                  15

Leu Val Ser Ile Leu Ser Phe Leu Leu Asp Leu Val Ala Asp Leu Trp
            20                  25                  30

Ala Val Val Gln Tyr Val Leu Leu Gly Arg Tyr Leu Trp Ala Ala Leu
        35                  40                  45

Val Leu Val Leu Leu Gly Gln Ala Ser Val Leu Leu Gln Leu Phe Ser
    50                  55                  60

Trp Leu Trp Leu Thr Ala Asp Pro Thr Glu Leu His His Ser Gln Leu
65                  70                  75                  80

Ser Arg Pro Phe Leu Ala Leu Leu His Leu Leu Gln Leu Gly Tyr Leu
                85                  90                  95

Tyr Arg Cys Leu His Gly Met His Gln Gly Leu Ser Met Cys Tyr Gln
            100                 105                 110

Glu Met Pro Ser Glu Cys Asp Leu Ala Tyr Ala Asp Phe Leu Ser Leu
        115                 120                 125

Asp Ile Ser Met Leu Lys Leu Phe Glu Ser Phe Leu Glu Ala Thr Pro
    130                 135                 140

Gln Leu Thr Leu Val Leu Ala Ile Val Leu Gln Asn Gly Gln Ala Glu
145                 150                 155                 160

Tyr Tyr Gln Trp Phe Gly Ile Ser Ser Phe Leu Gly Ile Ser Trp
                165                 170                 175

Ala Leu Leu Asp Tyr His Arg Ser Leu Arg Thr Cys Leu Pro Ser Lys
            180                 185                 190

Pro Arg Leu Gly Arg Ser Ser Ser Ala Ile Tyr Phe Leu Trp Asn Leu
```

```
            195                 200                 205
Leu Leu Leu Gly Pro Arg Ile Cys Ala Ile Ala Leu Phe Ser Ala Val
    210                 215                 220

Phe Pro Tyr Tyr Val Ala Leu His Phe Phe Ser Leu Trp Leu Val Leu
225                 230                 235                 240

Leu Phe Trp Ile Trp Leu Gln Gly Thr Asn Phe Met Pro Asp Ser Lys
                245                 250                 255

Gly Glu Trp Leu Tyr Arg Val Thr Met Ala Leu Ile Leu Tyr Phe Ser
                260                 265                 270

Trp Phe Asn Val Ser Gly Gly Arg Thr Arg Gly Arg Ala Val Ile His
            275                 280                 285

Leu Ile Phe Ile Phe Ser Asp Ser Val Leu Leu Val Thr Thr Ser Trp
290                 295                 300

Val Thr His Gly Thr Trp Leu Pro Ser Gly Ile Ser Leu Leu Met Trp
305                 310                 315                 320

Val Thr Ile Gly Gly Ala Cys Phe Phe Leu Gly Leu Ala Leu Arg Val
                325                 330                 335

Ile Tyr Tyr Leu Trp Leu His Pro Ser Cys Ser Trp Asp Pro Asp Leu
                340                 345                 350

Val Asp Gly Thr Leu Gly Leu Leu Ser Pro His Arg Pro Pro Lys Leu
            355                 360                 365

Ile Tyr Asn Arg Arg Ala Thr Leu Leu Ala Glu Asn Phe Phe Ala Lys
        370                 375                 380

Ala Lys Ala Arg Ala Val Leu Thr Glu Glu Val Gln Leu Asn Gly Val
385                 390                 395                 400

Leu

<210> SEQ ID NO 2
<211> LENGTH: 399
<212> TYPE: PRT
<213> ORGANISM: Rattus norvegicus

<400> SEQUENCE: 2

Met Pro Leu Ser Val His Pro Gln Val Ala Leu Asp Val Ile Gly
1               5                  10                  15

Leu Val Ser Thr Leu Ser Phe Leu Leu Asp Leu Val Ala Asp Leu Trp
                20                  25                  30

Ala Val Val Gln Tyr Val Leu Val Gly Arg Tyr Leu Trp Ala Ala Leu
                35                  40                  45

Val Val Val Leu Leu Gly Gln Ala Ser Val Leu Gln Leu Phe Ser
    50                  55                  60

Trp Leu Trp Leu Thr Ala Asp Pro Thr Glu Leu His Gln Leu Gln Pro
65                  70                  75                  80

Ser Arg Arg Phe Leu Ala Leu Leu His Leu Leu Gln Leu Gly Tyr Leu
                85                  90                  95

Tyr Arg Cys Leu His Gly Met Arg Gln Gly Leu Ser Met Cys Cys Gln
                100                 105                 110

Glu Val Pro Ser Glu Cys Asp Leu Ala Tyr Ala Asp Phe Leu Ser Leu
            115                 120                 125

Asp Ile Ser Met Leu Arg Leu Phe Glu Ser Phe Leu Glu Ala Thr Pro
        130                 135                 140

Gln Leu Thr Leu Val Leu Ala Ile Val Leu Gln Ser Gly Asn Ala Glu
145                 150                 155                 160

Tyr Tyr Gln Trp Phe Gly Ile Ser Ser Ser Phe Leu Gly Ile Ser Trp
```

```
            165                 170                 175
Ala Leu Leu Asp Tyr His Arg Ser Leu Arg Thr Cys Leu Pro Ser Lys
        180                 185                 190

Pro Arg Leu Gly Trp Cys Ser Ser Ala Val Tyr Phe Leu Trp Asn Leu
        195                 200                 205

Leu Leu Leu Gly Pro Arg Ile Cys Ala Ile Ala Thr Phe Ser Val Val
        210                 215                 220

Phe Pro Tyr Cys Leu Ala Leu His Phe Leu Ser Leu Trp Leu Val Leu
225                 230                 235                 240

Leu Tyr Trp Val Trp Leu Gln Asp Thr Lys Phe Met Pro Asn Ser Asn
            245                 250                 255

Gly Glu Trp Leu Tyr Arg Val Thr Val Ala Leu Ile Leu Tyr Phe Ser
            260                 265                 270

Trp Phe Asn Val Ser Gly Gly Arg Thr Gly Arg Ala Thr Ile His
        275                 280                 285

Leu Gly Phe Ile Leu Ser Asp Ser Val Leu Val Thr Thr Ser Trp
        290                 295                 300

Val Thr Asp Ser Thr Trp Leu Pro Gly Gly Val Leu Leu Trp Ala Ala
305                 310                 315                 320

Leu Gly Gly Ala Cys Phe Ser Leu Gly Leu Val Leu Arg Met Ile Tyr
                325                 330                 335

Tyr Leu Arg Leu His Pro Ser Cys Ser Trp Glu Pro Asp Phe Val Asp
                340                 345                 350

Gly Thr Leu Arg Leu Leu Pro Pro Glu Arg Pro Lys Leu Ile Tyr
            355                 360                 365

Asn Arg Arg Ala Thr Arg Leu Ala Gln Asn Phe Phe Ala Lys Leu Lys
            370                 375                 380

Thr Gln Ala Ala Leu Pro Gln Ala Val Gln Leu Asn Gly Val Leu
385                 390                 395

<210> SEQ ID NO 3
<211> LENGTH: 395
<212> TYPE: PRT
<213> ORGANISM: Homo sapiens

<400> SEQUENCE: 3

Met Pro Trp Ser Ser Arg Gly Ala Leu Leu Arg Asp Leu Val Leu Gly
1               5                   10                  15

Val Leu Gly Thr Ala Ala Phe Leu Leu Asp Leu Gly Thr Asp Leu Trp
            20                  25                  30

Ala Ala Val Gln Tyr Ala Leu Gly Gly Arg Tyr Leu Trp Ala Ala Leu
        35                  40                  45

Val Leu Ala Leu Leu Gly Leu Ala Ser Val Ala Leu Gln Leu Phe Ser
    50                  55                  60

Trp Leu Trp Leu Arg Ala Asp Pro Ala Gly Leu His Gly Ser Gln Pro
65              70                  75                  80

Pro Arg Arg Cys Leu Ala Leu Leu His Leu Gln Leu Gly Tyr Leu
            85                  90                  95

Tyr Arg Cys Val Gln Glu Leu Arg Gln Gly Leu Leu Val Trp Gln Gln
            100                 105                 110

Glu Glu Pro Ser Glu Phe Asp Leu Ala Tyr Ala Asp Phe Leu Ala Leu
        115                 120                 125

Asp Ile Ser Met Leu Arg Leu Phe Glu Thr Phe Leu Glu Thr Ala Pro
    130                 135                 140
```

Gln Leu Thr Leu Val Leu Ala Ile Met Leu Gln Ser Gly Arg Ala Glu
145                 150                 155                 160

Tyr Tyr Gln Trp Val Gly Ile Cys Thr Ser Phe Leu Gly Ile Ser Trp
            165                 170                 175

Ala Leu Leu Asp Tyr His Arg Ala Leu Arg Thr Cys Leu Pro Ser Lys
            180                 185                 190

Pro Leu Gly Leu Gly Ser Ser Val Ile Tyr Phe Leu Trp Asn Leu
        195                 200                 205

Leu Leu Leu Trp Pro Arg Val Leu Ala Val Ala Leu Phe Ser Ala Leu
        210                 215                 220

Phe Pro Ser Tyr Val Ala Leu His Phe Leu Gly Leu Trp Leu Val Leu
225                 230                 235                 240

Leu Leu Trp Val Trp Leu Gln Gly Thr Asp Phe Met Pro Asp Pro Ser
            245                 250                 255

Ser Glu Trp Leu Tyr Arg Val Thr Val Ala Thr Ile Leu Tyr Phe Ser
            260                 265                 270

Trp Phe Asn Val Ala Glu Gly Arg Thr Arg Gly Arg Ala Ile Ile His
        275                 280                 285

Phe Ala Phe Leu Leu Ser Asp Ser Ile Leu Leu Val Ala Thr Trp Val
290                 295                 300

Thr His Ser Ser Trp Leu Pro Ser Gly Ile Pro Leu Gln Leu Trp Leu
305                 310                 315                 320

Pro Val Gly Cys Gly Cys Phe Leu Gly Leu Ala Leu Arg Leu Val
            325                 330                 335

Tyr Tyr His Trp Leu His Pro Ser Cys Cys Trp Lys Pro Asp Pro Asp
            340                 345                 350

Gln Val Asp Gly Ala Arg Ser Leu Leu Ser Pro Glu Gly Tyr Gln Leu
            355                 360                 365

Pro Gln Asn Arg Arg Met Thr His Leu Ala Gln Lys Phe Pro Lys
        370                 375                 380

Ala Lys Asp Glu Ala Ala Ser Pro Val Lys Gly
385                 390                 395

<210> SEQ ID NO 4
<211> LENGTH: 410
<212> TYPE: PRT
<213> ORGANISM: Tetraodon nigroviridis

<400> SEQUENCE: 4

Met Arg Val Met Gly Gln Ala Thr Ile Ser Asn Tyr Ser Trp Ile Asp
1               5                   10                  15

Phe Val Phe Ser Val Ile Gly Val Phe Thr Phe Phe Val Asp Trp Gly
            20                  25                  30

Ala Asp Val Trp Val Ala Thr Glu Phe Tyr Ser Arg Gly Asp Phe Phe
            35                  40                  45

Trp Phe Gly Leu Leu Val Ser Leu Met Val Leu Ser Ser Val Leu Val
        50                  55                  60

Gln Met Phe Ser Trp Phe Trp Leu Lys Tyr Asp Arg Glu Leu Pro Asp
65              70                  75                  80

Val Cys Arg Gln Ser Gly Gly Gly Thr Val Leu Phe Gly Asp Arg Val
            85                  90                  95

Gln Leu Ser Trp Leu Leu His Val Leu Gln Leu Gly Phe Leu Cys Arg
            100                 105                 110

His Ile Ser Ala Ile Arg Gln Gly Phe Arg Val Trp Trp Arg Gln Gln
        115                 120                 125

```
Glu Gly Ser Glu Tyr Ala Val Tyr Leu Thr His Asp Leu Ser Met Leu
            130                 135                 140

Arg Leu Ile Glu Thr Phe Ser Glu Ser Ala Pro Gln Leu Thr Leu Met
145                 150                 155                 160

Val His Val Met Leu Cys Thr Asn Arg Ala Arg Thr Val Gln Ser Trp
                165                 170                 175

Met Val Val Asp Tyr His Arg Ser Leu Arg Ala Phe Leu Pro Asp Lys
                180                 185                 190

Ala Lys Gln Gly Trp Gly Ser Ser Leu Ile Tyr Phe Leu Trp Asn Phe
            195                 200                 205

Leu Leu Ile Ala Pro Arg Val Ala Ala Leu Ala Leu Phe Ala Ser Val
    210                 215                 220

Val Gly Gly Phe Val Ala Val His Phe Leu Leu Leu Trp Cys Val Phe
225                 230                 235                 240

Val Met Trp Ala Trp Leu Gln Gly Thr Glu Phe Met Asp Ser Val Cys
                245                 250                 255

Gly Glu Gly Leu Tyr Arg Ala Thr Val Gly Ile Ile Trp Tyr Phe Ser
            260                 265                 270

Trp Phe Asn Val Ala Glu Gly Gln Thr Arg Gly Arg Ser Ile Ile Tyr
        275                 280                 285

His Ser Phe Ile Thr Thr Asp Gly Gly Ile Leu Leu Leu Thr Trp Trp
    290                 295                 300

Cys Tyr Arg Asp Pro Val Gln Thr Glu Pro Tyr Gly Leu Ala Leu Leu
305                 310                 315                 320

Val Thr Leu Leu Phe Ser Tyr Leu Leu Gly Leu Leu Phe Lys Thr Val
                325                 330                 335

Tyr Tyr Cys Cys Phe His Pro Thr Met Arg Arg Pro Ala Arg Glu
            340                 345                 350

Ser Ser Asp Leu Pro Asp Ala Glu Val Thr Phe Arg His Phe Ser Ile
        355                 360                 365

Gln Asp Gly Ala Pro Ser Ser Pro Leu Leu Asn Arg Arg Met Ala Ala
    370                 375                 380

His Ala Ala Arg Phe Tyr Ser Glu Arg Arg Ala Val Lys Asn Leu Gly
385                 390                 395                 400

Gly Val Asp Ala Ala Thr Ser Ser Pro Pro
                405                 410

<210> SEQ ID NO 5
<211> LENGTH: 383
<212> TYPE: PRT
<213> ORGANISM: Oryzias latipes

<400> SEQUENCE: 5

Met Ala Val Phe Thr Phe Ser Pro Leu Asp Phe Val Phe Ser Cys Leu
1               5                   10                  15

Gly Leu Pro Leu Phe Leu Ala Asp Val Val Leu Asp Val Leu Ala Val
            20                  25                  30

Ile Asp Phe Tyr Lys Glu Glu Ala Trp Val Arg Leu Ser Val Leu Leu
        35                  40                  45

Leu Leu Leu Val Gly Ser Ser Val Leu Ile Gln Val Tyr Ser Trp Lys
    50                  55                  60

Trp Tyr Ile Gly Asp Gly Leu Asp Leu Lys Thr Arg Val Glu Ser Ala
65                  70                  75                  80

Leu Lys Lys Gly Leu Lys Thr Leu His Val Leu Gln Leu Gly Ile Tyr
```

```
                85                  90                  95
Val Arg His Leu Gly Val Leu Glu Lys Ser Val Ser Gly Phe Cys Gly
            100                 105                 110

Lys Gly Ser Asp Ser Gln Asn Ser Lys Asp Val Ala Val Glu Leu Ser
        115                 120                 125

His Asp Leu Cys Met Leu His Leu Ile Glu Thr Phe Ser Glu Ser Ala
    130                 135                 140

Pro Gln Ile Val Leu Trp Leu Thr Ile Ile Leu Gln Asp Gly Lys Leu
145                 150                 155                 160

Asp Asp Ser Asn Gln Leu Ser Ile Ile Ser Ile Ile His Phe Leu
                165                 170                 175

Trp Asn Leu Leu Leu Leu Ser Arg Leu Thr Ala Leu Ala Leu Phe
                180                 185                 190

Ala Ser Val Leu Pro Cys Phe Ile Phe Thr His Val Phe Cys Cys Trp
            195                 200                 205

Met Val Phe Val Leu Phe Ala Trp Arg Ala Gln Thr Asp Phe Met Asp
        210                 215                 220

Asp Pro Trp Gly Glu Arg Leu Tyr Arg Ala Thr Val Ala Leu Ile Trp
225                 230                 235                 240

Tyr Phe Asp Trp Phe Asn Val Phe Lys Lys Arg Thr Lys Lys Ser Ala
                245                 250                 255

Leu Leu Tyr His Ser Phe Ile Leu Leu Asp Thr Cys Met Leu Cys Gly
                260                 265                 270

Leu Trp Phe Trp Arg Met Asn Thr His Pro Pro Gln Phe Val Ile Pro
        275                 280                 285

Arg Pro Tyr Ala Asp Val Met Ala Ser Ser Val Val Ala Val Tyr Ile
        290                 295                 300

Leu Gly Leu Met Val Lys Ala Leu Tyr Tyr Arg Phe Phe His Pro Lys
305                 310                 315                 320

His Asn Gln Asp Asn Leu Arg Gly Glu Asp Gln Asn Glu Val Ser Gly
                325                 330                 335

Gln Asn Asn Asp Thr Arg Arg Glu Arg Asp Glu Thr Asp Gly Thr Met
            340                 345                 350

Met Met Arg Met Met Val Ser Ser Pro Ala Pro Leu Arg Gln Thr Gln
        355                 360                 365

Asn Gly Lys Lys Arg Met Arg Met Leu Ala Glu Asn Phe Tyr Ser
        370                 375                 380

<210> SEQ ID NO 6
<211> LENGTH: 410
<212> TYPE: PRT
<213> ORGANISM: Xenopus laevis

<400> SEQUENCE: 6

Met Pro Ala Cys Cys Pro Pro Arg Tyr Arg Leu Leu Asp Leu Val Phe
1               5                   10                  15

Ala Leu Gly Gly Thr Leu Thr Phe Leu Leu Asp Leu Gly Ser Asp Val
            20                  25                  30

Trp Gly Ala Leu Ala Tyr Tyr Arg Ala Gly Asp Val Ala Trp Ala Ala
        35                  40                  45

Leu Leu Ile Gly Phe Tyr Gly Met Ala Ser Leu Val Leu Gln Leu His
    50                  55                  60

Ser Trp Gly Trp Phe Trp Thr Asp Arg Arg Ser Gly Asn Ile Trp Glu
65                  70                  75                  80
```

-continued

Leu Pro Arg Asp Pro His Arg Ala Gly Ser Gly Ser Ala Ser Thr
            85                  90                  95

Tyr Thr Glu Arg Gly Pro Gly Glu Leu Asn Ala Arg Gly Ser Ala Ser
        100                 105                 110

Cys Gly Cys Ile His Ser Leu Glu Val Gly Ile Ala Ala Tyr Arg Ser
            115                 120                 125

Ser Glu Asn Asn Pro Thr Tyr Asp Arg Tyr Gln Glu Tyr Ala Tyr Phe
130                 135                 140

Leu Thr His Asp Ile Ser Met Met Arg Leu Met Glu Thr Phe Leu Glu
145                 150                 155                 160

Asn Thr Pro Gln Leu Ile Leu Leu Tyr Ile Val Leu His Arg Gly
                165                 170                 175

Thr Ile Tyr Thr Phe Gln Tyr Phe Ser Ile Ser Ile Ser Phe Ile Ser
            180                 185                 190

Ile Ser Trp Ala Ile Leu Asp Tyr His Gln Ser Leu Arg Leu Phe Leu
        195                 200                 205

Lys Asp Lys Gln Ser Met Asn Ile Leu Ser Ser Ile Ile Tyr Phe Leu
    210                 215                 220

Trp Asn Leu Leu Leu Ile Phe Ser Arg Ile Val Cys Ile Thr Leu Phe
225                 230                 235                 240

Ile Ser Val Phe His Leu Trp Val Ala Leu His Phe Leu Leu Leu Trp
                245                 250                 255

Ile Ala Phe Phe Leu Trp Ala Thr Trp Gln Ser Thr Asp Phe Met Arg
            260                 265                 270

Asn Arg Ile Leu Glu His Phe Phe Arg Ala Thr Val Ala Val Ile Leu
        275                 280                 285

Tyr Phe Ser Trp Phe Asn Ile Ala Asp Gly Arg Thr Ile Tyr Arg Cys
    290                 295                 300

Ile Val Tyr Tyr Cys Phe Ile Thr Ala Asp Ser Val Ile Leu Phe Met
305                 310                 315                 320

Ser Trp Lys Ile Phe Lys Phe Pro Ser Ile Leu Asp Glu Tyr Glu Thr
                325                 330                 335

Tyr Leu Leu Tyr Val Leu Ala Val Phe Phe Pro Val Gly Ile Leu Phe
            340                 345                 350

Arg Val Leu Tyr Tyr Leu Tyr Leu His Pro Asn Leu Gln Lys Lys Lys
        355                 360                 365

Lys Lys Lys Glu Met Tyr Asp Glu Pro Asp Gly Leu Met Ser Asp Ala
    370                 375                 380

Asn Gly Tyr Arg Leu Leu Lys Arg Glu Pro Val Met Leu Lys Asn Pro
385                 390                 395                 400

Arg Ile Ile Gln Leu Ser Met Gln Leu Met
                405                 410

<210> SEQ ID NO 7
<211> LENGTH: 33
<212> TYPE: DNA
<213> ORGANISM: Artificial Sequence
<220> FEATURE:
<223> OTHER INFORMATION: Synthetic primer

<400> SEQUENCE: 7
atatggatcc atcatgcctc tgtccgtgca cca          33

<210> SEQ ID NO 8
<211> LENGTH: 30
<212> TYPE: DNA

```
<213> ORGANISM: Artificial Sequence
<220> FEATURE:
<223> OTHER INFORMATION: Synthetic primer

<400> SEQUENCE: 8
atatgaattc gaggactcca ttcagctgca                                    30

<210> SEQ ID NO 9
<211> LENGTH: 33
<212> TYPE: DNA
<213> ORGANISM: Artificial Sequence
<220> FEATURE:
<223> OTHER INFORMATION: Synthetic primer

<400> SEQUENCE: 9
atatggatcc gccatgccct ggtcgtcccg cgg                                33

<210> SEQ ID NO 10
<211> LENGTH: 30
<212> TYPE: DNA
<213> ORGANISM: Artificial Sequence
<220> FEATURE:
<223> OTHER INFORMATION: Synthetic primer

<400> SEQUENCE: 10
atatgaattc tcccttcact ggcgaagcag                                    30

<210> SEQ ID NO 11
<211> LENGTH: 30
<212> TYPE: DNA
<213> ORGANISM: Artificial Sequence
<220> FEATURE:
<223> OTHER INFORMATION: Synthetic primer

<400> SEQUENCE: 11
gggaccctgc cctcgtggct gggaccctag                                    30

<210> SEQ ID NO 12
<211> LENGTH: 30
<212> TYPE: DNA
<213> ORGANISM: Artificial Sequence
<220> FEATURE:
<223> OTHER INFORMATION: Synthetic primer

<400> SEQUENCE: 12
ctagggtccc agccacgagg gcagggtccc                                    30

<210> SEQ ID NO 13
<211> LENGTH: 30
<212> TYPE: DNA
<213> ORGANISM: Artificial Sequence
<220> FEATURE:
<223> OTHER INFORMATION: Synthetic primer

<400> SEQUENCE: 13
aagcccgacc ctgcccaggt agccggggcc                                    30

<210> SEQ ID NO 14
<211> LENGTH: 30
<212> TYPE: DNA
<213> ORGANISM: Artificial Sequence
<220> FEATURE:
<223> OTHER INFORMATION: Synthetic primer

<400> SEQUENCE: 14
ggccccggct acctgggcag ggtcgggctt                                    30
```

<210> SEQ ID NO 15
<211> LENGTH: 37
<212> TYPE: DNA
<213> ORGANISM: Artificial Sequence
<220> FEATURE:
<223> OTHER INFORMATION: Synthetic primer

<400> SEQUENCE: 15
cgagatctga attctcagtc tacctggtca gggtcgg                             37

<210> SEQ ID NO 16
<211> LENGTH: 29
<212> TYPE: DNA
<213> ORGANISM: Artificial Sequence
<220> FEATURE:
<223> OTHER INFORMATION: Target sequence for shRNA

<400> SEQUENCE: 16
gaatctgtgc catcgccttg ttctcagct                                      29

<210> SEQ ID NO 17
<211> LENGTH: 25
<212> TYPE: DNA
<213> ORGANISM: Artificial Sequence
<220> FEATURE:
<223> OTHER INFORMATION: Synthetic primer

<400> SEQUENCE: 17
ctcattgctg atgtgggtga caata                                          25

<210> SEQ ID NO 18
<211> LENGTH: 25
<212> TYPE: DNA
<213> ORGANISM: Artificial Sequence
<220> FEATURE:
<223> OTHER INFORMATION: Synthetic primer

<400> SEQUENCE: 18 aggctttct ctactttga tggag                                            25

<210> SEQ ID NO 19
<211> LENGTH: 25
<212> TYPE: DNA
<213> ORGANISM: Artificial Sequence
<220> FEATURE:
<223> OTHER INFORMATION: Synthetic primer

<400> SEQUENCE: 19
cattatcttc ctcactggct gaatc                                          25

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
ttagggatta gaatgtgttt                                                20

<210> SEQ ID NO 21
<211> LENGTH: 20
<212> TYPE: DNA
<213> ORGANISM: Artificial Sequence
<220> FEATURE:

<223> OTHER INFORMATION: Synthetic primer

<400> SEQUENCE: 21
cctatacaaa taacccaact                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
gcgacgccac agctcacact                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
ccccagcagc agcaggttcc                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
agcaggcatc tgagggccca                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic primer

<400> SEQUENCE: 25
gagagcaatg ccagccccgg                                                    20

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
aggccgggcc atcatccact                                                    20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
tgcgcctgtt ctgaggcagc                                                    20

```
<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
gcatcctcac cctgaagtac                                                      20

<210> SEQ ID NO 29
<211> LENGTH: 21
<212> TYPE: DNA
<213> ORGANISM: Artificial Sequence
<220> FEATURE:
<223> OTHER INFORMATION: Synthetic primer

<400> SEQUENCE: 29
cttaatgtca cgcacgattt c                                                    21
```